(12) United States Patent
Liu et al.

(10) Patent No.: US 7,608,591 B2
(45) Date of Patent: Oct. 27, 2009

(54) TARGETED DELIVERY TO LEGUMAIN-EXPRESSING CELLS

(75) Inventors: Cheng Liu, Carlsbad, CA (US); Thomas S. Edgington, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 265 days.

(21) Appl. No.: 11/288,978

(22) Filed: Nov. 29, 2005

(65) Prior Publication Data

US 2006/0135410 A1 Jun. 22, 2006

Related U.S. Application Data

(63) Continuation of application No. PCT/US2004/017157, filed on May 28, 2004.
(60) Provisional application No. 60/474,840, filed on May 29, 2003.

(51) Int. Cl.
*A61K 38/00* (2006.01)
*A61K 38/14* (2006.01)
*C07K 9/00* (2006.01)
*A61K 38/04* (2006.01)

(52) U.S. Cl. .............. 514/18; 514/8; 514/17; 530/322; 530/330

(58) Field of Classification Search .............. None
See application file for complete search history.

(56) References Cited

U.S. PATENT DOCUMENTS

| | | | |
|---|---|---|---|
| 4,036,945 A | 7/1977 | Haber | |
| 4,317,815 A * | 3/1982 | Coy et al. .......... | 514/15 |
| 4,331,647 A | 5/1982 | Goldenberg | |
| 4,472,509 A | 9/1984 | Gansow et al. | |
| 4,507,232 A * | 3/1985 | Tamai et al. ........ | 530/331 |
| 4,816,567 A | 3/1989 | Cabilly et al. | |
| 4,938,949 A | 7/1990 | Borch et al. | |
| 4,946,778 A | 8/1990 | Ladner et al. | |
| 4,980,464 A * | 12/1990 | Naito et al. ........ | 540/222 |
| 5,021,236 A | 6/1991 | Gries et al. | |
| 6,004,933 A | 12/1999 | Spruce et al. | |
| 6,051,230 A | 4/2000 | Thorpe et al. | |
| 6,245,750 B1 | 6/2001 | Shepard | |
| 6,506,559 B1 | 1/2003 | Greenwald et al. | |
| 6,545,131 B1 | 4/2003 | Isaacs et al. | |
| 6,624,142 B2 | 9/2003 | Fire et al. | |
| 6,625,142 B1 | 9/2003 | Joffe et al. | |
| 6,683,061 B1 | 1/2004 | Shepard et al. | |
| 6,720,306 B2 | 4/2004 | Greenwald et al. | |
| 2002/0147138 A1 | 10/2002 | Firestone et al. | |
| 2003/0054387 A1 | 3/2003 | Chen et al. | |
| 2003/0216298 A1 | 11/2003 | Gengrinovitch | |
| 2006/0251663 A1* | 11/2006 | Mariscal-Gonzalez et al. ............. | 424/159.1 |

FOREIGN PATENT DOCUMENTS

| | | |
|---|---|---|
| EP | 0045665 A1 | 2/1982 |
| EP | 0404097 A2 | 12/1990 |
| WO | WO-93/11161 A1 | 6/1993 |
| WO | WO-98/13059 A1 | 4/1998 |
| WO | WO-00/64945 A1 | 11/2000 |
| WO | WO-01/07454 A1 | 2/2001 |
| WO | WO-01/62300 A2 | 8/2001 |
| WO | WO-01/85960 A1 | 11/2001 |
| WO | WO-02/20715 A2 | 3/2002 |
| WO | WO-02/096910 A1 | 12/2002 |
| WO | WO-03/016335 A2 | 2/2003 |
| WO | WO03098991 * | 12/2003 |
| WO | WO-2004/111192 A2 | 12/2004 |

OTHER PUBLICATIONS

Hong et al. Formulation, stability, and antitumor activity of 1-beta-D-arabinofuranosylcytosine conjugate of thioether phospholipid. Cancer Research. Jul. 15, 1990. 50. 4401-4406.*
Merrifield. Concept and Early Development of Solid-Phase Peptide Synthesis. Methods in Enzymology. 1997. vol. 289. pp. 3-13.*
Albini, A., "A Rapid in Vitro Assay for Quantitating the Invasive Potential of Tumor Cells", *Cancer Research*, 47(2), (Jun. 15, 1987), 3239-3245.
Almquist, R. G., et al., "Synthesis and Biological Activity of a Ketomethylene Analogue of a Tripeptide Inhibitor of Angiotensin Converting Enzyme", *Journal of Medicinal Chemistry*, 23, (1980), 1392-1398.
Alvarez-Fernandez, M., et al., "Inhibition of Mammalian Legumain by Some Cystatins Is Due to a Novel Second Reactive Site", *The Journal of Biological Chemistry*, 274(27), (1999), 19195-19203.
Asgian, J. L., et al., "Aza-Peptide Epoxides: A New Class of Inhibitors Selective for Clan CD Cysteine Proteases", *Journal of Medicinal Chemistry*, 45(23), (2002), 4958-4960.
Barrett, A. J., et al., "Evolutionary Lines of Cysteine Peptidases", *Biological Chemistry*, 382, (2001), 727-733.
Beck, H., et al., "Cathepsin S and an Asparagine-Specific Endoprotease Dominate the Proteolytic Processing of Human Myelin Basis Protein in vitro", *European Journal of Immunology*, 31, (2001), 3726-3736.
Bird, R. E., "Single-Chain Antigen-Binding Proteins", *Science*, 242(4877), (Oct. 21, 1988), 423-426.
Bretscher, M. S., et al., "Membrane Traffic During Cell Locomotion", *Current Opinion in Cell Biology*, 10, (1998), 537-541.
Castino, R., et al., "Lysosomal Proteases as Potential Targets for the Induction of Apoptotic Cell Death in Human Neuroblastomas", *International Journal of Cancer*, 97, (2002), 775-779.
Chakravarty, P. K., et al., "Plasmin-Activated Prodrugs for Cancer Chemotherapy, 2. Synthesis and Biological Activity of Peptidyl Derivatives of Doxorubicin", *Journal of Medicinal Chemistry*, 26, (1983), 638-644.
Chambers, A. F., et al., "Changing Views of the Role of Matrix Metalloproteinases in Metastasis", *Journal of the National Cancer Institute*, 89(17), (1977), 1260-1270.

(Continued)

*Primary Examiner*—Cecilia Tsang
*Assistant Examiner*—Marcela M Cordero Garcia
(74) *Attorney, Agent, or Firm*—Schwegman, Lundberg & Woessner, P.A.

(57) ABSTRACT

The present invention relates to new agents and methods useful for preventing, treating and diagnosing diseases such as cancer. For example, the invention relates to prodrug agents useful for targeting and delivering cytotoxic drugs to cancerous cells.

17 Claims, 8 Drawing Sheets

OTHER PUBLICATIONS

Chang, C., et al., "The Many Faces of Metalloproteases: Cell Growth, Invasion, Angiogenesis and Metastasis", *Trends in Cell Biology*, 11(11), (2001),S37-S43.

Chen, J.-M., et al., "Activation of Progelatinase A by Mammalian Legumain, a Recently Discovered Cysteine Proteinase", *Biological Chemistry*, 382, (2001), 777-783.

Chen, J.-M., et al., "Cloning and Expression of Mouse Legumain, a Lysosomal Endopeptidase", *The Biochemical Journal*, 335 (Part 1), (1998), 111-117.

Chen, J.-M. , et al., "Cloning, Isolation, and Characterization of Mammalian Legumain, an Asparaginyl Endopeptidase", *The Journal of Biological Chemistry*, 272(12), (1997),8090-8098.

Choi, S. J., et al., "Identification of Human Asparaginyl Endopeptidase (Legumain) as an Inhibitor of Osteoclast Formation and Bone Resorption", *The Journal of Biological Chemistry*, 274, (1999) , 27747-27753.

Choi, S. J., et al., "Osteoclast Inhibitory Peptide 2 Inhibits Osteoclast Formation via Its C-Terminal Fragment", *Journal of Bone and Mineral Research*, 16(10), (2001), 1840-1811.

Chothia, C., "Domain Association in Immunoglobulin Molecules. The Packing of Variable Domains", *Journal of Molecular Biology*. 186(3), (1985) , 651-663.

Clackson, T., "Making Antibody Fragments Using Phage Display Libraries", *Nature*, 352(6336), (Aug. 15, 1991), 624-628.

Coulibaly, S., et al., "Modulation of Invasive Properties of Murine Squamous Carcinoma Cells by Heterologous Expression of Cathepsin B and Cystatin C", *International Journal of Cancer*, 83, (1999), 526-531.

De Groot, F. M., et al., "Synthesis and Biological Evaluation of Novel Prodrugs of Anthracyclines for Selective Activation by the Tumor-Associated Protease Plasmin", *Journal of Medicinal Chemistry*, 42(25), (1999), 5277-5283.

De Jong, J., et al., "Analysis and Pharmacokinetics of N-l-leucyldoxorubicin and Metabolites in Tissues of Tumor-Bearing BALB/c Mice", *Cancer Chemotherapy and Pharmacology*, 31, (1992), 156-160.

Denmeade, S. R., et al., "Enzymatic Activation of a Doxorubicin-Peptide Prodrug by Prostate-Specific Antigen", *Cancer Research*, 58(12), (1998), 2537-2540.

Dubowchik, G. M., et al., "Cathepsin B-Sensitive Dipeptide Prodrugs. 2. Models of Anticancer Drugs Paclitaxel (Taxol®), Mitomycin C and Doxorubicin", *Bioorganic & Medicinal Chemistry Letters*, 8, (1998), 3347-3352.

Dubowchik, G. M., et al., "Cathepsin B-Sensitive Dipeptide Prodrugs. 1. A Model Study of Structural Requirements for Efficient Release of Doxorubicin", *Bioorganic & Medicinal Chemistry Letters* 8, (1998), 3341-3346.

Elbashir, S. M., et al., "Analysis of Gene Function in Somatic Mammalian Cells Using Small Interfering RNAs", *Methods*, 26(2), (2002), 199-213.

Foghsgaard, L., et al., "Cathepsin B Acts as a Dominant Execution Protease in Tumor Cell Apoptosis Induced by Tumor Necrosis Factor", *The Journal of Cell Biology*, 153(5), (2001), 999-1009.

Gravesen, A., et al., "Restriction Fragment Differential Display of Pediocin- Resistant *Listeria monocytogenes* 412 Mutants Shows Consistent Overexpression of a Putative β-Glucoside-Specific PTS System", *Microbiology*, 146 (*Part* 6), (2000), 1381-1389.

Hanahan, D., "The Hallmarks of Cancer", *Cell*, 100, (2000), 57-70.

Hann, M. M., et al., "On the Double Bond Isostere of the Peptide Bond: Preparation of an Enkephalin Analgoue", *Journal of Chemical Society—Perkin Transactions* 1, No. 1, (1982), 307-314.

Hashimoto, S.-I., et al., "Serial Analysis of Gene Expression in Human Monocytes and Macrophages", *Blood*, 94(3), (1999), 837-844.

Holladay, M. W., et al., "Synthesis of Hydroxyethylene and Ketomethylene Dipeptide Isosteres", *Tetrahedron Letters*, 24 (41), (1983), 4401-4404.

Holliger, P., ""Diabodies": Small Bivalent and Bispecific Antibody Fragments", *Proc. Natl. Acad. Sci. USA*, 90(14), (Jul. 15, 1993), 6444-6448.

Holmes, M. A., "Structural Consequences of Humanizing an Antibody", *Journal of Immunology*. 158(5), (1997), 2192-2201.

Hruby, V. J., "Conformational Restrictions of Biologically Active Peptides via Amino Acid Side Chain Groups", *Life Sciences*, 31(3), (1982), 189-199.

Hudson, D., et al., "Methionine Enkephalin and Isosteric Analogues", *International Journal of Peptide and Protein Research*, 14(3), (1979), 177-185.

Itoh, Y., et al., "Plasma Membrane-Bound Tissue Inhibitor of Metalloproteinases (TIMP)-2 Specifically Inhibits Matrix Metalloproteinase 2 (Gelatinase A) Activated on the Cell Surface", *The Journal of Biological Chemistry*, 273(38), (1998), 24360-24367.

Jennings-White, C. , et al., "Synthesis of Ketomethylene Analogs of Dipeptides", *Tetrahedron Letters*, 23(25), (1982), 2533-2534.

Jones, P. T., "Replacing the Complementarity-Determining Regions in a Human Antibody With Those From a Mouse", *Nature*, 321(6069), (May 29, 1986), 522-525.

Köhler, G., "Continuous Cultures of Fused Cells Secreting Antibody of Predefined Specificity", *Nature*, 256(5517), (Aug. 7, 1975), 495-497.

Liu, C., "Overexpression of Legumain in Tumors Is Significant for Invasion/ Metastasis and a Candidate Enzymatic Target for Prodrug Therapy", *Cancer Research* 63, (Jun. 1, 2003), 2957-2964.

Mai, J., et al., "Human Procathepsin B Interacts With the Annexin II Tetramer on the Surface of Tumor Cells", *The Journal of Biological Chemistry*, 275, (2000), 12806-12812.

Manoury, B., et al., "An Asparaginyl Endopeptidase Processes a Microbial Antigen for Class II MHC Presentation", *Nature*, 396, (1998), 695-699.

Marks, J. D., "By-passing Immunization. Human Antibodies From V-Gene Libraries Displayed on Phage", *Journal of Molecular Biology*. 222(3), (1991), 581-597.

Martinez, L. A., et al., "Synthetic Small Inhibiting RNAs: Efficient Tools to Inactivate Oncogenic Mutations and Restore p53 Pathways", *Proc. Natl. Acad. Sci. USA*, 99(23), (Nov. 12, 2002), 14849-14854.

Mathieu, M. A., et al., "Substrate Specificity of Schistosome Versus Human Legumain Determined by P1-P3 Peptide Libraries", *Molecular & Biochemical Parasitology*, 121(1), (2002), 99-105.

Merrifield, R. B., "Solid Phase Peptide Synthesis. I. The Synthesis of a Tetrapeptide", *The Journal of the American Chemical Society*, 85(14), (Jul. 20, 1963), 2149-2154.

Morley, J. S., "Modulation of the Action of Regulatory Peptides by Structural Modification", *Trends in Pharmacological Sciences*, 1(2), (1980), 463-468.

Morrison, S, L., "Chimeric Human Antibody Molecules: Mouse Antigen- Binding Domains With Human Constant Region Domains", *Proc. Natl. Acad. Sci. USA*, 81(21), (Nov. 1984), 6851-6855.

Nabi, I. R., "The Polarization of the Motile Cell", *Journal of Cell Science*, 112, (1999), 1803-1811.

Nagase, H., "Activation Mechanisms of Matrix Metalloproteinases", *Biological Chemistry*, 378, (1997), 151-160.

Niestroj, A. J., et al., "Inhibition of Mammalian Legumain by Michael Acceptors and AzaAsn-Halomethylketones", *Biological Chemistry*, 383(7-8),. (Jul./Aug. 2002), 1205-1214.

Novotny, J., et al., "Structural Invariants of Antigen Binding: Comparison of Immunoglobulin $V_L$-$V_H$ and $V_L$-$V_L$ Domain Dimers", *Proc. Natl. Acad. Sci. USA*, 82(14), (Jul. 15, 1985),4592-4596.

Pack, P., "Improved Bivalent Miniantibodies, With Identical Avidity as Whole Antibodies, Produced by High Cell Density Fermentation of *Escherichia coli*", *Bio/Technology*. 11(11), (Nov. 1993), 1271-1277.

Paddison, P. J., et al., "RNA Interference: The New Somatic Cell Genetics?", *Cancer Cell*, 2(1), (Jul. 2002), 17-23.

Paddison, P. J., et al., "Short Hairpin RNAs (shRNAs) Induce Sequence- Specific Silencing in Mammalian Cells", *Genes and Development*, 16(8), (2002), 948-958.

Payne, G., "Progress in Immunoconjugate Cancer Therapeutics", *Cancer Cell*, 3, (Mar. 2003), 207-212.

Presta, L. G., "Antibody Engineering", *Current Opinion in Structural Biology*, 2(4): (1992), 593-596.

Riechmann, L., "Reshaping Human Antibodies for Therapy.", *Nature*, 332(6162), (Mar. 24, 1988),323-327.

Satchi, R., et al., "PDEPT: Polymer-Directed Enzyme Prodrug Therapy. I. HPMA Copolymer-Cathepsin B and PK1 as a Model Combination", *British Journal of Cancer*, 85(7), 2001, 1070-1076.

Scherr, M., et al., "Gene Silencing Mediated by Small Interfering RNAs in Mammalian Cells", *Current Medicinal Chemistry*, 10, (2003), 245-256.

Schwarz, G., et al., "Characterization of Legumain", *Biological Chemistry*, 383, (Nov. 2002), 1813-1816.

Sexton, P. S., et al., "Inhibition of Motility and Invasion of B16 Melanoma by the Overexpression of Cystatin C", *Melanoma Research*, 7(2), (1997), 97-101.

Shang, X.-Z., et al., "Enhancement of Monocyte Transendothelial Migration by Granulocyte-Macrophage Colony-Stimulating Factor: Requirement for Chemoattractant and CD11a/CD18 Mechanisms", *European Journal of Immunology*, 29(11), (1999), 3571-3582.

Spatola, A. F., et al., "Structure-Activity Relationships of Enkephalins Containing Serially Replaced Thiomethylene Amide Bond Surrogates", *Life Sciences*, 38(14), (1986), 1243-1249.

Sporn, M. B., "The War on Cancer", *The Lancet*, 347, (1996),1377-1381.

Stetler-Stevenson, M. G., "Matrix Metalloproteinases in Angiogenesis: A Moving Target for Therapeutic Intervention", *The Journal of Clinical Investigation*, 103(9), (May 1999),1237-1241.

Storch, H., et al., "Tierexperimentelle Untersuchungen zur Immunogenität, humoraler Nachweisreaktion and Anaphylaxiegefahr bei parenteraler Hyaluronidasegabe", *Zeitschrift für experimentelle Chirurgie*, 11(2), (1978),128-133.

Theilβen, G., et al., "RC4D—Restriction Fragment Length Polymorphism- Coupled Domain-Directed Differential Display", *Methods in Molecular Biology*, 85, (1997), 123-133.

Vaswani, S. K., "Humanized Antibodies as Potential Therapeutic Drugs", *Annals of Allergy, Asthma, & Immunology*, 81 (2), (1998), 105-119.

Wang, J. M., et al., "Induction of Monocyte Migration by Recombinant Macrophage Colony-Stimulating Factor", The Journal of Immunology, 141(2), (1988), 575-579.

Werb, Z., "ECM and Cell Surface Proteolysis: Regulating Cellular Ecology", *Cell*, 91, (Nov. 14, 1997),439-442.

Wrang, M. L., et al., "Changes in Gene Expression Following Induction of Ischemic Tolerance in Rat Brain: Detection and Verification", Journal of *Neuroscience Resarch*, 65, (2001), 54-58.

Yano, M., "Expression of Cathepsin B and Cystatin C in Human Breast Cancer", *Surgery Today*, 31(5), (2001), 385-389.

Yonezawa, S., et al., "Structures of the Proteolytic Processing Region of Cathepsin D", *The Journal of Biological Chemistry*, 263(31), (1988), 16504-16509.

Zhang, J. S., et al., "Differential Display of mRNA", *Molecular Biotechnology*, 10(2), (1998), 155-165.

Zhu, D.-M., et al., "Cathepsin Inhibition Induces Apoptotic Death in Human Leukemia and Lymphoma Cells", *Leukemia and Lymphoma*, 39(3-4), (2000), 343-354.

"International Application Serial No. 2004248318, First Examiner's Report mailed Mar. 17, 2008", 1 pg.

Manfredini, Stefano, et al., "Peptide T-araC Conjugates: Solid-Phase Synthesis and Biological Activity of N4-(Acylpeptidyl)-araC", *Bioorganic & Medicinal Chemistry* (8), (2000), 539-547.

Wu, W., et al., "Targeting Cell-Impermeable Prodrug Activiation to Tumor Microenvironment Eradicates Multiple Drug-Resistant Neoplasms", *Cancer Res.*, 66(2), (2006), 970-980.

\* cited by examiner

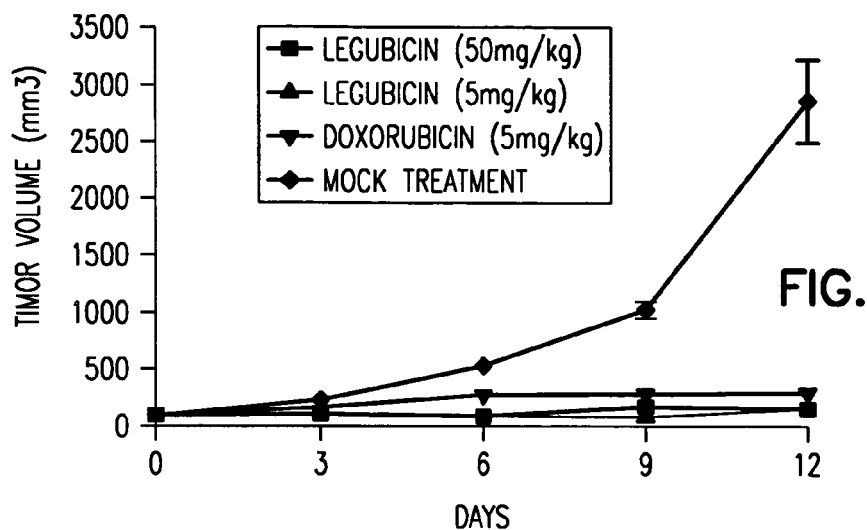
FIG. 6A1
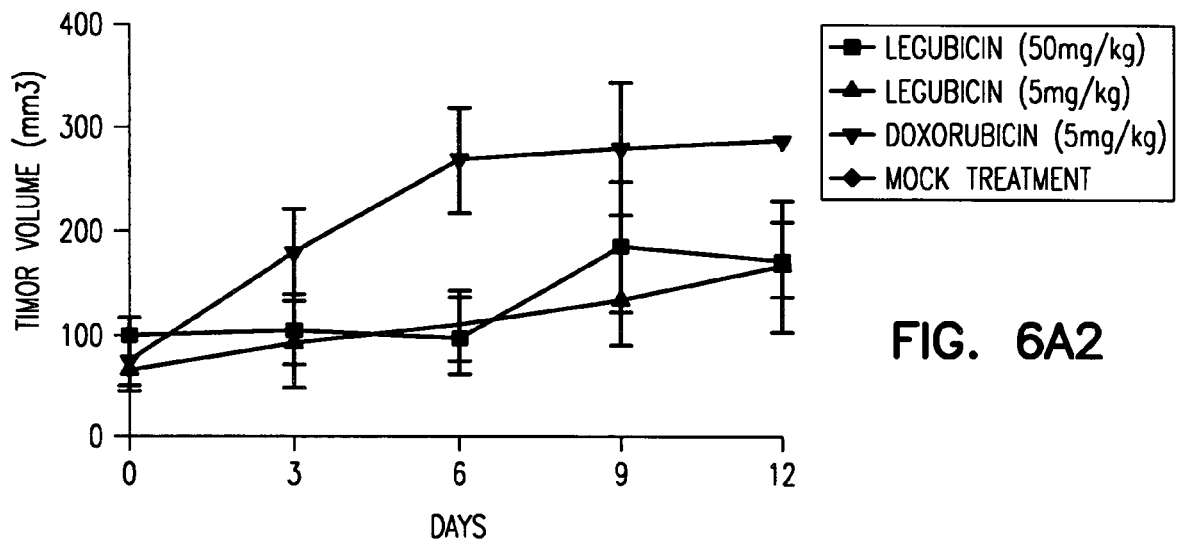
FIG. 6A2
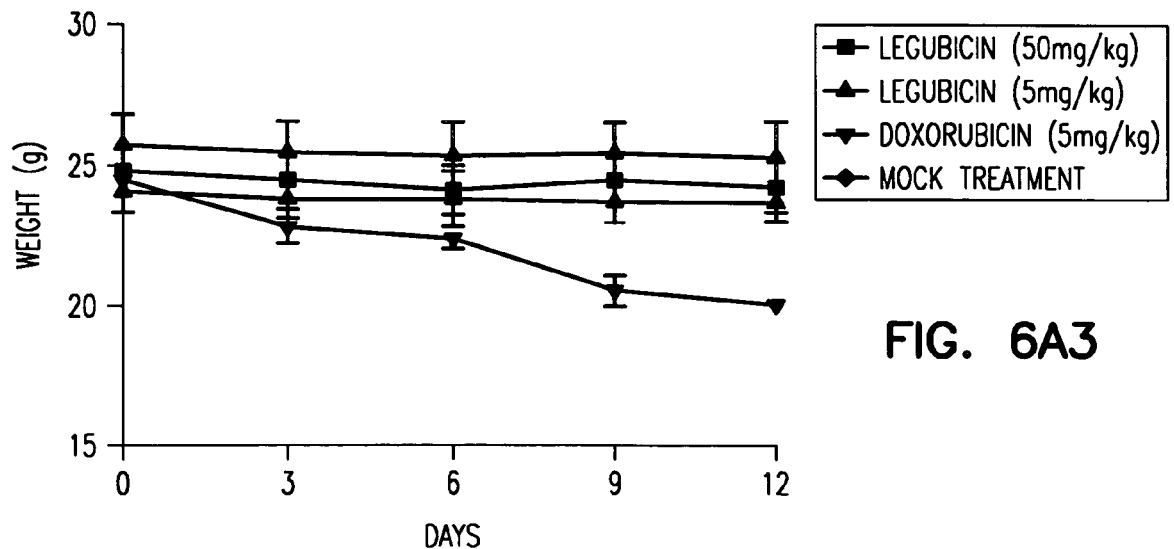
FIG. 6A3

SEQUENCE LISTING

<160> NUMBER OF SEQ ID NOS: 15

<210> SEQ ID NO 1
<211> LENGTH: 433
<212> TYPE: PRT
<213> ORGANISM: Homo sapiens

<400> SEQUENCE: 1

Met Val Trp Lys Val Ala Val Phe Leu Ser Val Ala Leu Gly Ile Gly
 1               5                   10                  15

Ala Ile Pro Ile Asp Asp Pro Glu Asp Gly Gly Lys His Trp Val Val
             20                  25                  30

Ile Val Ala Gly Ser Asn Gly Trp Tyr Asn Tyr Arg His Gln Ala Asp
         35                  40                  45

Ala Cys His Ala Tyr Gln Ile Ile His Arg Asn Gly Ile Pro Asp Glu
     50                  55                  60

Gln Ile Val Val Met Met Tyr Asp Asp Ile Ala Tyr Ser Glu Asp Asn
65                  70                  75                  80

Pro Thr Pro Gly Ile Val Ile Asn Arg Pro Asn Gly Thr Asp Val Tyr
                 85                  90                  95

Gln Gly Val Pro Lys Asp Tyr Thr Gly Glu Asp Val Thr Pro Gln Asn
            100                 105                 110

Phe Leu Ala Val Leu Arg Gly Asp Ala Glu Ala Val Lys Gly Ile Gly
        115                 120                 125

Ser Gly Lys Val Leu Lys Ser Gly Pro Gln Asp His Val Phe Ile Tyr
    130                 135                 140

Phe Thr Asp His Gly Ser Thr Gly Ile Leu Val Phe Pro Asn Glu Asp
145                 150                 155                 160

Leu His Val Lys Asp Leu Asn Glu Thr Ile His Tyr Met Tyr Lys His

```
                        165                 170                 175
Lys Met Tyr Arg Lys Met Val Phe Tyr Ile Glu Ala Cys Glu Ser Gly
                180                 185                 190
Ser Met Met Asn His Leu Pro Asp Asn Ile Asn Val Tyr Ala Thr Thr
            195                 200                 205
Ala Ala Asn Pro Arg Glu Ser Ser Tyr Ala Cys Tyr Tyr Asp Glu Lys
        210                 215                 220
Arg Ser Thr Tyr Leu Gly Asp Trp Tyr Ser Val Asn Trp Met Glu Asp
225                 230                 235                 240
Ser Asp Val Glu Asp Leu Thr Lys Glu Thr Leu His Lys Gln Tyr His
                245                 250                 255
Leu Val Lys Ser His Thr Asn Thr Ser His Val Met Gln Tyr Gly Asn
            260                 265                 270
Lys Thr Ile Ser Thr Met Lys Val Met Gln Phe Gln Gly Met Lys Arg
        275                 280                 285
Lys Ala Ser Ser Pro Val Pro Leu Pro Pro Val Thr His Leu Asp Leu
        290                 295                 300
Thr Pro Ser Pro Asp Val Pro Leu Thr Ile Met Lys Arg Lys Leu Met
305                 310                 315                 320
Asn Thr Asn Asp Leu Glu Glu Ser Arg Gln Leu Thr Glu Glu Ile Gln
                325                 330                 335
Arg His Leu Asp Ala Arg His Leu Ile Glu Lys Ser Val Arg Lys Ile
            340                 345                 350
Val Ser Leu Leu Ala Ala Ser Glu Ala Glu Val Glu Gln Leu Leu Ser
        355                 360                 365
Glu Arg Ala Pro Leu Thr Gly His Ser Cys Tyr Pro Glu Ala Leu Leu
    370                 375                 380
His Phe Arg Thr His Cys Phe Asn Trp His Ser Pro Thr Tyr Glu Tyr
385                 390                 395                 400
Ala Leu Arg His Leu Tyr Val Leu Val Asn Leu Cys Glu Lys Pro Tyr
                405                 410                 415
Pro Leu His Arg Ile Lys Leu Ser Met Asp His Val Cys Leu Gly His
            420                 425                 430
Tyr

<210> SEQ ID NO 2
<211> LENGTH: 1981
<212> TYPE: DNA
<213> ORGANISM: Homo sapiens

<400> SEQUENCE: 2
ggcacgaggg aggctgcgag ccgccgcgag ttctcacggt cccgccggcg ccaccaccgc      60
ggtcactcac cgccgccgcc gccaccactg ccaccacggt cgcctgccac aggtgtctgc     120
aattgaactc caaggtgcag atggtttgg aaagtagctg tattcctcag tgtggccctg      180
ggcattggtg ccattcctat agatgatcct gaagatggag gcaagcactg ggtggtgatc     240
gtggcaggtt caaatggctg gtataattat aggcaccagg cagacgcgtg ccatgcctac     300
cagatcattc accgcaatgg gattcctgac aacagatcg ttgtgatgat gtacgatgac      360
attgcttact ctgaagacaa tcccactcca ggaattgtga tcaacaggcc aatggcaca     420
gatgtctatc agggagtccc gaaggactac actggagagg atgttacccc acaaaatttc     480
cttgctgtgt tgagaggcga tgcagaagca gtgaagggca taggatccgg caaagtcctg     540
aagagtggcc cccaggatca cgtgttcatt tacttcactg accatggatc tactggaata     600
```

```
ctggttttc ccaatgaaga tcttcatgta aggacctga atgagaccat ccattacatg    660
tacaaacaca aaatgtaccg aaagatggtg ttctacattg aagcctgtga gtctgggtcc    720
atgatgaacc acctgccgga taacatcaat gtttatgcaa ctactgctgc aaccccaga    780 gagtcgtcct acgcctgtta ctatgatgag aagaggtcca cgtacctggg ggactggtac    840
agcgtcaact ggatggaaga ctcggacgtg aagatctga ctaaagagac cctgcacaag    900
cagtaccacc tggtaaaatc gcacaccaac accagccacg tcatgcagta tggaaacaaa    960
acaatctcca ccatgaaagt gatgcagttt cagggtatga acgcaaagc cagttctccc    1020 gtccccctac ctccagtcac acaccttgac ctcacccca gccctgatgt gcctctcacc    1080
atcatgaaaa ggaaactgat gaacaccaat gatctggagg agtccaggca gctcacggag    1140
gagatccagc ggcatctgga tgccaggcac ctcattgaga agtcagtgcg taagatcgtc    1200
tccttgctgg cagcgtccga ggctgaggtg gagcagctcc tgtccgagag agccccgctc    1260
acggggcaca gctgctaccc agaggccctg ctgcacttcc ggacccactg cttcaactgg    1320
cactccccca cgtacgagta tgcgttgaga catttgtacg tgctggtcaa cctttgtgag    1380
aagccgtatc cacttcacag gataaaattg tccatggacc acgtgtgcct tggtcactac    1440
tgaagagctg cctcctggaa gcttttccaa gtgtgagcgc cccaccgact gtgtgctgat    1500
cagagactgg agaggtggag tgagaagtct ccgctgctcg ggccctcctg gggagccccc    1560
gctccagggc tcgctccagg accttcttca caagatgact tgctcgctgt tacctgcttc    1620
cccagtcttt tctgaaaaac tacaaattag ggtgggaaaa gctctgtatt gagaagggtc    1680
atatttgctt tctaggaggt ttgttgtttt gcctgttagt tttgaggagc aggaagctca    1740
tgggggcttc tgtagccct ctcaaaagga gtctttattc tgagaatttg aagctgaaac    1800
ctctttaaat cttcagaatg attttattga agagggccgc aagccccaaa tggaaaactg    1860
tttttagaaa atatgatgat ttttgattgc ttttgtattt aattctgcag gtgttcaagt    1920
cttaaaaaat aaagatttat aacagaaccc aaaaaaaaaa aaaaaaaaaa aaaaaaaaa    1980 a                                                                   1981
```

<210> SEQ ID NO 3
<211> LENGTH: 4
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1,2
<223> OTHER INFORMATION: Xaa = any amino acid
<220> FEATURE:
<221> NAME/KEY: SITE
<222> LOCATION: 4
<223> OTHER INFORMATION: Xaa = is either absent or is any amino acid
      that has no substantial effect on the activity of the drug

<400> SEQUENCE: 3

Xaa Xaa Asn Xaa
 1

<210> SEQ ID NO 4
<211> LENGTH: 4
<212> TYPE: PRT
<213> ORGANISM: Artificial Sequence
<220> FEATURE:
<223> OTHER INFORMATION: A synthetic prodrug amino acid sequence
<220> FEATURE:

```
<221> NAME/KEY: SITE
<222> LOCATION: 1
<223> OTHER INFORMATION: Xaa = Boc-Ala

<400> SEQUENCE: 4

Xaa Ala Asn Leu
 1

<210> SEQ ID NO 5
<211> LENGTH: 4
<212> TYPE: PRT
<213> ORGANISM: Artificial Sequence
<220> FEATURE:
<223> OTHER INFORMATION: A synthetic prodrug amino acid sequence

<400> SEQUENCE: 5

Ala Ala Asn Leu
 1

<210> SEQ ID NO 6
<211> LENGTH: 4
<212> TYPE: PRT
<213> ORGANISM: Artificial Sequence
<220> FEATURE:
<223> OTHER INFORMATION: A synthetic prodrug amino acid sequence

<400> SEQUENCE: 6

Ala Thr Asn Leu
 1

<210> SEQ ID NO 7
<211> LENGTH: 4
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
<223> OTHER INFORMATION: Xaa = Boc-Ala

<400> SEQUENCE: 7

Xaa Ala Asn Leu
 1

<210> SEQ ID NO 8
<211> LENGTH: 4
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
<223> OTHER INFORMATION: Xaa = N-Succinyl-Ala

<400> SEQUENCE: 8

Xaa Ala Asn Leu
 1

<210> SEQ ID NO 9
<211> LENGTH: 4
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
```

```
<223> OTHER INFORMATION: Xaa = N-(-t-Butoxycarbonyl)-Ala

<400> SEQUENCE: 9

Xaa Thr Asn Leu
 1

<210> SEQ ID NO 10
<211> LENGTH: 4
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
<223> OTHER INFORMATION: Xaa = N-Succinyl-Ala

<400> SEQUENCE: 10

Xaa Thr Asn Leu
 1

<210> SEQ ID NO 11
<211> LENGTH: 3
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
<223> OTHER INFORMATION: Xaa = N-(-t-Butoxycarbonyl)-Ala

<400> SEQUENCE: 11

Xaa Asn Leu
 1

<210> SEQ ID NO 12
<211> LENGTH: 3
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
<223> OTHER INFORMATION: Xaa = N-Succinyl-Ala

<400> SEQUENCE: 12

Xaa Asn Leu
 1

<210> SEQ ID NO 13
<211> LENGTH: 2
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
<223> OTHER INFORMATION: Xaa = N-(t-Butoxycarbonyl)-Thr

<400> SEQUENCE: 13

Xaa Leu
 1

<210> SEQ ID NO 14
<211> LENGTH: 2
<212> TYPE: PRT
```

```
-continued

<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 1
<223> OTHER INFORMATION: Xaa=N-Succinyl-Thr

<400> SEQUENCE: 14

Xaa Leu
 1

<210> SEQ ID NO 15
<211> LENGTH: 5
<212> TYPE: PRT
<213> ORGANISM: Artificial Sequence
<220> FEATURE:
<223> OTHER INFORMATION: A synthetic prodrug amino acid sequence
<220> FEATURE:
<221> NAME/KEY: SITE
<222> LOCATION: 3
<223> OTHER INFORMATION: Xaa = beta-Asn

<400> SEQUENCE: 15

Ala Leu Xaa Ala Ala
 1               5
```

TARGETED DELIVERY TO LEGUMAIN-EXPRESSING CELLS

RELATED APPLICATIONS

This application is a continuation under 35 U.S.C. 111(a) of International Application No. PCT/US2004/017157 filed May 28, 2004 and published in English as WO 2004/111192 A3 on Dec. 23, 2004, which claims the benefit of U.S. Application Ser. No. 60/474,840 filed May 29, 2003. The contents of both these applications are incorporated by reference herein in their entireties.

STATEMENT OF GOVERNMENT RIGHTS

The invention was made with the support of a grant from the Government of the United States of America (Grant Number P01 HL 16411 from the National Institutes of Health). The Government may have certain rights to the invention.

FIELD OF THE INVENTION

The present invention relates to legumain expressing cells and new agents that can target legumain expressing cells. In some embodiments, the invention relates to prodrug agents useful for targeting and delivering cytotoxic agents to cancerous cells or tumor cells that express legumain.

BACKGROUND OF THE INVENTION

The following description includes information that may be useful in understanding the present invention. It is not an admission that any of the information provided herein is prior art, or relevant, to the presently described inventions, or that any publication or document that is specifically or implicitly referenced is prior art.

According to the National Cancer Institute, since 1990 over 17 million people have been diagnosed with cancer, and an additional 1,334,100 new cancer cases are expected to be diagnosed in 2003. About 556,500 Americans are expected to die of cancer in 2003, more than 1500 people every day. Cancer is the second leading cause of death in the United States, exceeded only by heart disease. The National Institutes of Health estimate the overall costs of cancer in the year 2002 at $171.6 billion (Cancer Facts & Figures, 2003). Clearly, cancer is an enormous problem, and cancer treatments are needed.

Current cancer treatments generally involve the use of surgery, radiation therapy, and/or chemotherapy. However, these treatments all involve serious side effects. For example, surgery can be complicated by bleeding, damage to internal organs, adverse reactions to anesthesia or other medicines, pain, infection, and slow recovery. Radiation therapy can damage normal cells and can cause fatigue. For many people chemotherapy is the best option for controlling their cancer. However, chemotherapy can also damage normal cells such as bone marrow and blood cells, cells of the hair follicles, and cells of the reproductive and digestive tracts. Chemotherapy can also cause nausea, vomiting, constipation, diarrhea, fatigue, changes to the nervous system, cognitive changes, lung damage, reproductive and sexual problems, liver, kidney, and urinary system damage, and, especially with the use of the chemotherapeutic agent doxorubicin, heart damage. Long-term side effects of chemotherapy can include permanent organ damage, delayed development in children, nerve damage, and blood in the urine. Thus, the use of the chemotherapy for cancer treatment is not without serious side effects.

Most agents currently administered to a patient are not targeted to the site where they are needed, resulting in systemic delivery of the agent to cells and tissues of the body where the agent is unnecessary, and often undesirable. Such systemic delivery may result in adverse side effects, and often limits the dose of an agent (e.g., cytotoxic agents and other anti-cancer agents) that can be administered. Accordingly, a major goal has been to develop methods for specifically targeting agents to cancerous cells and tissues.

Thus, it would be desirable to be able to direct various agents to cancer cells so as to be able to decrease the dosage of the agents given and to decrease the systemic toxicity and side effects associated with the agents.

Accordingly, there is a need for methods to target agents to cancerous cells.

SUMMARY OF THE INVENTION

According to the invention, an unexpectedly high level expression of legumain, an asparaginyl endopeptidase, is present in a wide variety of cancer cells. As described herein, legumain expression is also associated with increased cancer cell invasion and metastasis. Legumain expression is also associated with reduced cancer cell apoptosis. The invention provides agents to treat cancerous cells and tissues that utilize legumain as a cancer marker and an indicator of metastasis. In one embodiment, the invention relates to a legumain-activated prodrug that is tumoricidal in vivo, with reduced side effects and toxicity relative to currently available chemotherapeutics. These agents are useful not only to treat cancer, but also useful to treat other conditions associated with legumain expression in tissues and cells.

Accordingly, in some embodiments, the present invention provides a prodrug compound, including a drug molecule linked to a peptide, wherein the peptide has an amino acid sequence that includes at least two linked amino acids, wherein at least one of the two linked amino acids is Asn, and wherein legumain cleaves the peptide at the covalent linkage between the Asn and another amino acid to generate an active drug from the prodrug. The prodrug is substantially non-toxic to normal animal cells, whereas the drug is an active drug that can have a beneficial effect upon an animal to which it is administered. Such a compound can be, for example, N-(succinyl-L-Ala-L-Ala-L-Asn-L-Leu)doxorubicin.

The drug employed is any drug whose action is diminished or blocked by attachment of a peptide to the drug. In some embodiments, the drug can be a cytotoxin. Such a cytotoxin can be aldesleukin, asparaginase, bleomycin sulfate, camptothecin, carboplatin, carmustine, cisplatin, cladribine, lyophilized cyclophosphamide, non-lyophilized cyclophosphamide, cytarabine, dacarbazine, dactinomycin, daunorubicin, diethylstilbestrol, epoetin alfa, esperamycin, etidronate, etoposide, filgrastim, floxuridine, fludarabine phosphate, fluorouracil, goserelin, granisetron hydrochloride, idarubicin, ifosfamide, immune globulin, interferon alpha-2a, interferon alpha-2b, leucovorin calcium, leuprolide, levamisole, mechlorethamine, medroxyprogesterone, melphalan, methotrexate, mitomycin, mitoxantrone, octreotide, ondansetron hydrochloride, paclitaxel, pamidronate, disodium, pegaspargase, plicamycin, sargramostim, streptozocin, taxol, thiotepa, teniposide, vinblastine, or vincristine. In some embodiments, the drug is doxorubicin.

The prodrug can have a peptide amino acid sequence of the prodrug can be SEQ ID NO:3:

Pr-(Xaa1)$_n$-Xaa2-Asn-(Xaa3)-drug wherein:
Pr is a protecting group;
n is an integer of about 0 to about 50;
Xaa1 and Xaa2 are separately any amino acid;
Xaa3 is either nothing or an amino acid that has no substantial effect on the activity of the drug; and the drug employed is a drug whose action is diminished or blocked by attachment of a peptide to the drug.

Examples of peptide sequences that may be used include amino acid sequence Asn-Leu, Ala-Asn-Leu, Thr-Asn-Leu, Ala-Ala-Asn-Leu (SEQ ID NO:5), Ala-Thr-Asn-Leu (SEQ ID NO:6), and Boc-Ala-Ala-Asn-Leu (SEQ ID NO:4). Examples of prodrugs provided by the invention include Boc-Ala-Ala-Asn-Leu-doxorubicin (SEQ ID NO:7), succinyl-Ala-Ala-Asn-Leu-doxorubicin (SEQ ID NO:8), N-(-t-Butoxycarbonyl-Ala-Thr-Asn-Leu)doxorubicin (SEQ ID NO:9), N-(Succinyl-Ala-Thr-Asn-Leu)doxorubicin (SEQ ID NO:10), N-(-t-Butoxycarbonyl-Ala-Asn-Leu)doxorubicin (SEQ ID NO:11), N-(Succinyl-Ala-Asn-Leu)doxorubicin (SEQ ID NO:12), N-(-t-Butoxycarbonyl-Thr-Leu)doxorubicin (SEQ ID NO:13), N-(Succinyl-Thr-Leu)doxorubicin (SEQ ID NO:14), A variety of protecting groups can be utilized, for example, in some embodiments the protecting group is an amino protecting group. In other embodiments, the protecting group is succinyl, t-butoxycarbonyl. The peptide further can, for example, have an N-β-alanyl terminus.

The invention also provides a pharmaceutical composition that includes at least one of the prodrug compounds of the invention and a pharmaceutically acceptable carrier.

The invention also provides a method for treating a mammal having, or suspected of having cancer. The method includes administering to the mammal a prodrug compound of the invention in amounts and at intervals effective to prevent, reduce, or eliminate one or more of the symptoms associated with cancer. Cancers that can be treated by the invention include solid tumors and cancers as well as cancers associated with particular tissues, including breast cancer, colon cancer, lung cancer, prostate cancer, ovarian cancer, cancer of the central nervous system, lymphoma, or melanoma. The cancer can, for example, be autoimmune deficiency syndrome-associated Kaposi's sarcoma, cancer of the adrenal cortex, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries.

The invention also provides a method for imaging a tissue, that includes contacting a test tissue suspected of including legumain with of an agent that specifically binds to legumain, and detecting whether the agent binds to the test tissue. The method can further include quantifying and comparing amounts of the agent bound to the test tissue with amounts of the agent bound to a control tissue that does not comprise legumain. The agent can be an antibody that specifically binds to legumain.

The invention also provides a method for diagnosing cancer in a tissue that includes contacting the tissue with of an agent that specifically binds to legumain, and detecting whether the agent binds to the tissue. The invention also provides a method for diagnosing cancer in an animal that includes administering to the animal an agent that specifically binds to legumain, and detecting whether the agent accumulates in a tissue. These methods can further include diagnosing the patient as having or not having cancer.

The invention also provides a method for inhibiting cancer metastasis in an animal, including administering a compound or prodrug of the invention to the animal in amounts and at intervals effective to prevent, reduce, or eliminate cancer metastasis.

The invention also provides a method for inhibiting cell migration in an animal that includes administering a compound or prodrug of the invention to the animal in amounts and at intervals effective to prevent, reduce, or eliminate cancer cell migration.

The invention also provides a method of killing a cell in a tissue, including contacting the cell with a compound or prodrug of the invention in amounts and at intervals effective to kill the cell, wherein the tissue can be legumain.

The invention also provides a method for treating cancer in animal that includes administering to the animal a compound of the invention that inhibits legumain in amounts and at intervals effective to prevent, reduce, or eliminate one or more symptoms of cancer in the animal.

The invention also provides a method for inhibiting cancer metastasis in a tissue that includes contacting the tissue with a compound that inhibits legumain in amounts and at intervals effective to prevent, reduce, or eliminate cancer metastasis.

The invention also provides a method for inhibiting cancer cell migration in a tissue that includes contacting the tissue with a compound that inhibits legumain in amounts and at intervals effective to prevent, reduce, or eliminate cancer cell migration.

The invention also provides a method for treating inflammation in an animal, which includes administering to the mammal a compound that inhibits legumain in amounts and at intervals effective to prevent, reduce, or eliminate one or more symptoms associated with cancer.

The invention also provides a method for delivering a drug to a legumain-expressing cell in a mammal, which includes administering to the mammal an effective amount of a drug attached an agent that binds to legumain. The agent that binds to legumain can be a legumain inhibitor, a legumain substrate, an anti-legumain antibody or other agent that can bind to legumain.

The invention also provides a legumain inhibitor having including formula III or IV:

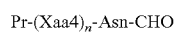
Pr-(Xaa4)$_n$-Asn-CHO     III

Xaa4-Asn-Y     IV wherein:

Pr is a protecting group;

n is an integer of about 2 to about 5;

Xaa4 is an amino acid or an amino acid mimetic;

Y is alkyl or alkenyl, optionally substituted with 1-3 halo or hydroxy, alkylamino, dialkylamino, alkyldialkylamino, or cycloalkyl, alkylcycloalkyl, alkenylcycloalkyl, aryl; ($C_5$-$C_{12}$)arylalkyl or ($C_5$-$C_{12}$)arylalkenyl, wherein the aryl groups of the arylalky or arylalkenyl can be 0-4 heteroatoms selected from N, O and S, and are optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, ($C_5$-$C_6$)aryl, —O—($C_5$-$C_6$)aryl, arylcarboxamide, alkylthio or haloalkylthio; and wherein the inhibitor is capable of binding to legumain.

In other embodiments, the legumain inhibitor can be cystatin, stefin, a peptide including the sequence Ala-Leu-β-Asn-Ala-Ala (SEQ ID NO:15) or an antibody that inhibits legumain activity.

In another embodiment, the compounds of the invention can be used for the manufacture of a medicament useful for treating diseases such as cancer.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 1A provides doubly-stained section of CT26 mouse colon cancer. Legumain stained red and CD31+ endothelial cells stained green in the original (magnification 600×). Legumain expression was high in tumor cells. Endothelial cells also expressed legumain. Legumain appeared to be largely in membranous vesicles, consistent with a distribution of endosomes/lysosomes. Legumain was also detected on the surface of tumor cells and endothelial cells (arrows). FIG. 1B provides a western blot analysis of legumain expression. Lanes 1-9 are brain, tumor, lung, heart, muscle, intestine, spleen, liver, and kidney, respectively. Legumain expression is high in tumor tissues (lane 2). Legumain expression in normal tissues is highest in kidney (lane 9), followed by liver (lane 8) and spleen (lane 7). FIG. 1C illustrates whether legumain expression can be detected with anti-legumain antisera in the following normal human tissues: kidney, adrenal gland, bone marrow, lymph, muscle, ovary, colon, lung and prostate (magnifications 200×). FIG. 1D illustrates whether legumain expression can be detected with anti-legumain antisera in the following normal human tissues: cerebellum, liver, heart, esophagus, pancreas, peripheral nerve, stomach, testis and thyroid (magnifications 200×). FIG. 1E illustrates whether leguman expression can be detected with anti-legumain antisera in the following tumor specimens: breast cancer, CNS cancer, lymphoma, and melanoma (magnification 400×). FIG. 1F illustrates whether leguman expression can be detected with anti-legumain antisera in the following tumor specimens: colon cancer, lung cancer, ovarian cancer, and prostate cancer (magnification 400×).

FIG. 2A shows that legumain is detected in intracellular vesicles (lighter areas; green staining in the original). FIG. 2B shows that legumain is prominently associated with the invadopodia of migrating tumor cells (arrows). FIG. 2C shows that legumain is also observed on cell surface of serum starved BEND3 cells (arrows). FIG. 2D shows that legumain is associated with the actin cortex (arrows). FIG. 2E show doubly-stained legumain$^+$ 293 cells where legumain stained in red and integrin β1 stained in green in the original. Legumain appeared in granular organelles that resemble aggregated lysosomes, as well as on the cell surface, co-localizing with β1 integrins (arrow). Magnification 1,000×. FIG. 2F illustrates the conversion of a 72 kDa progelatinase A to the 62 kDa active enzyme by legumain. Activation was minimal in reaction with control 293 cells (lane 1), but a majority of this zymogen was converted to active when reacted with legumain$^+$ 293 cells (lane 2). Activation was fully inhibited by cystatin (lane 3). FIG. 2G illustrates that legumain was not active against progelatinase B (lane 4 and lane 5 are progelatinase B with 293 cells and legumain+ 293 cells, respectively).

FIG. 3A illustrates that the migration of legumain+ 293 cells was markedly greater than the migration of control 293 cells. The enhanced cell migration was partially inhibited by cystatin, but not by TIMP-2 or E64. FIG. 3B shows that legumain enhanced 293 cell invasion across a matrigel barrier as compared to control 293 cells that did not overexpress legumain. The invasive activity was partially inhibited by cystatin and TIMP-2, but was not affected by the presence of E64. Each bar represented the mean±SE of three independent wells, and the experiments were repeated at least three times with similar results. p<0.001.

FIG. 4A illustrates that distant metastases were detected in 50% of WEHI nude mice inoculated with 293 cells that over-expressed legumain as compared to mice inoculated with wild type 293 cells. FIG. 4B provides a photomicrograph of a section of a tumor generated in WEHI nude mice with legumain$^+$ 293 cells. FIG. 4C provides a photomicrograph of a section of a tumor generated by control 293 cells. Note that the pseudo-encapsulation seen in the typical control 293 cell tumors (arrows) was lacking in legumain$^+$ 293 cell tumors. Moreover, 293 tumor invasion of muscle was frequent in mice receiving legumain$^+$ 293 cells (arrows, FIG. 4B). Magnification 200×.

FIGS. 6A-E illustrate the tumoricidal effect of legubicin on CT26 colon carcinoma in vivo. FIGS. 6A1-6A3 graphically illustrate the in vivo effect of legubicin on CT26 colon carcinoma tumor volume (FIG. 6A1 and 6A2) and animal weight (FIG. 6A3). Three intraperitoneal injections at both 5 mg/kg and 50 mg/kg were administered with 2 day intervals. Legubicin arrested tumor growth and tumor eradication was achieved (FIG. 6A1 and 6A2) with little evidence of toxicity, as indicated by animal weight loss (FIG. 6A3). In contrast, doxorubicin caused the death of the host animals at 5 mg/kg. FIG. 6A2 is a graph of the same experiment presented in FIG. 6A1 without data from the mock treated control group. FIG. 6B provides a photomicrograph of a H&E stained tumor section, where the animal had been treated with legubicin (magnification 1320×). FIG. 6C provides a photomicrograph of a H&E stained tumor section, where the animal had been treated with equivalent dose of doxorubicin (magnification 1320x). FIG. 6D provides a photomicrograph of a tumor section that had been subjected to a TUNEL assay, where the tumor specimens were treated with legubicin (magnification 400×). FIG. 6E provides a photomicrograph of a tumor section that had been subjected to a TUNEL assay, where the tumor specimens were treated with doxorubicin (magnification 400×). As shown in FIGS. 6D and 6E, tumors treated with legubicin have a higher apoptotic index than tumors treated with doxorubicin (see arrows).

DETAILED DESCRIPTION OF THE INVENTION

Figure 1A:
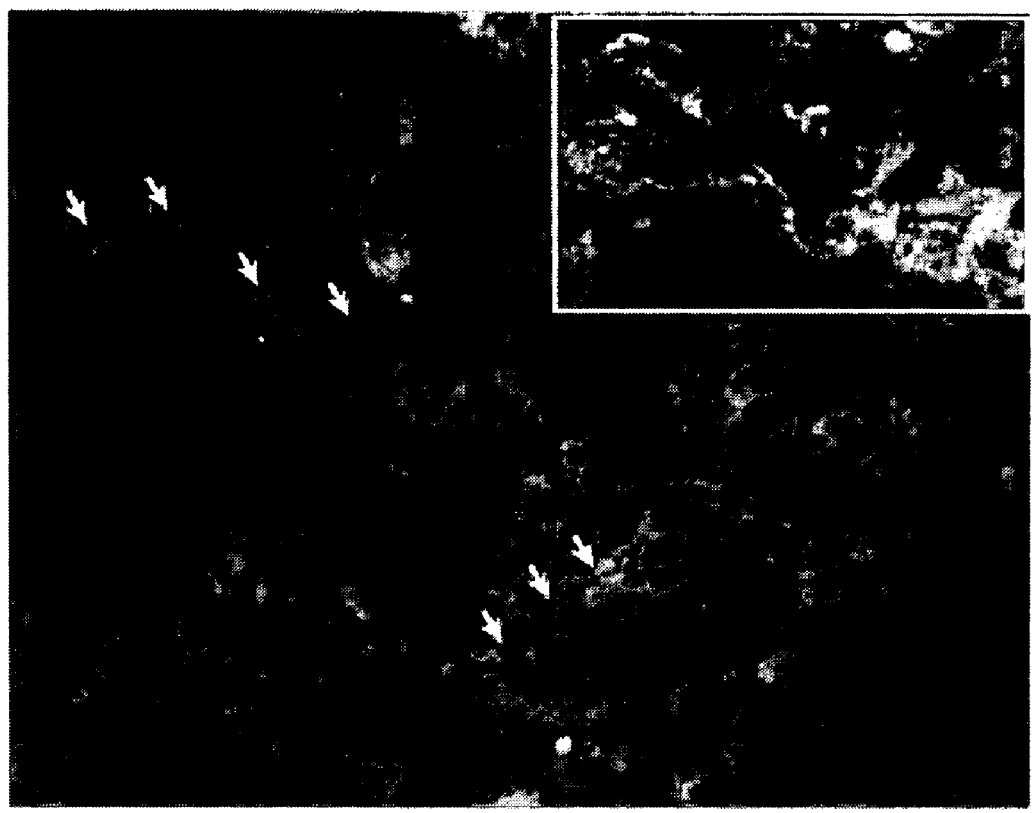
FIG. 1A-F illustrates that legumain is over-expressed in tumors.

The invention provides compositions and methods for targeting agents to cancerous cells. The agents may be drugs, cytotoxic agents or agents useful for imaging and diagnosis. The invention is based upon a discovery that legumain, a novel asparaginyl endopeptidase, is preferentially expressed in tumors. As shown herein, legumain was detected in membrane-associated vesicles concentrated at the invadopodia of tumor cells, and, unexpectedly, on cell surfaces where it co-localized with integrins. Cells that over-expressed legumain possessed increased migratory and invasive activity in vitro, and adopted an invasive and metastatic phenotype in vivo. Accordingly, legumain may have a role in tumor invasion and metastasis. The invention also provides prodrugs that include a legumain-cleavable peptide linked to a cytotoxic agent. An exemplary prodrug agent, designated legubicin, exhibited reduced toxicity and enhanced tumoricidal activity in vivo in a murine colon carcinoma model relative to doxorubicin.

Legumain

Legumain is a lysosomal protease, and a member of the C13 family of cysteine proteases (Chen et al., 1997). Legumain is evolutionarily conserved and is present in plants, invertebrate parasites, as well as in mammals. An example of an amino acid sequence for a preproprotein of a human legumain can be found in the National Center for Biotechnology Information (NCBI) database (http://www.ncbi.nlm.nih.gov/) at accession number NP 005597 (gi: 21914881), and is reproduced below (SEQ ID NO:1).

```
  1 MVWKVAVFLS  VALGIGAIPI  DDPEDGGKHW  VVIVAGSNGW
 41 YNYRHQADAC  HAYQIIHRNG  IPDEQIVVMM  YDDIAYSEDN
 81 PTPGIVINRP  NGTDVYQGVP  KDYTGEDVTP  QNFLAVLRGD
121 AEAVKGIGSG  KVLKSGPQDH  VFIYFTDHGS  TGILVFPNED
161 LHVKDLNETI  HYMYKHKMYR  KMVFYIEACE  SGSMMNHLPD
201 NINVYATTAA  NPRESSYACY  YDEKRSTYLG  DWYSVNWMED
241 SDVEDLTKET  LHKQYHLVKS  HTNTSHVMQY  GNKTISTMKV
281 MQFQGMKRKA  SSPVPLPPVT  HLDLTPSPDV  PLTIMKRKLM
321 NTNDLEESRQ  LTEETQRHLD  ARHLIEKSVR  KIVSLLAASE
361 AEVEQLLSER  APLTGHSCYP  EALLHFRTHC  FNWHSPTYEY
401 ALRHLYVLVN  LCEKPYPLHR  IKLSMDHVCL  GHY
```

An example of a nucleotide sequence for a human legumain that encodes SEQ ID NO:1 can found in the NCBI database at accession number NM_005606 (gi: 21914880). This nucleotide sequence is reproduced below (SEQ ID NO:2).

```
  1 GGCACGAGGG  AGGCTGCGAG  CCGCCGCGAG  TTCTCACCGT
 41 CCCGCCGGCG  CCACCACCGC  GGTCACTCAC  CGCCGCCGCC
 81 GCCACCACTG  CCACCACGGT  CGCCTGCCAC  AGGTGTCTGC
121 AATTGAACTC  CAAGGTGCAG  AATGGTTTGC  AAACTAGCTG
161 TATTCCTCAG  TGTGGCCCTG  GGCATTGGTG  CCATTCCTAT
201 AGATGATCCT  GAAGATGGAG  GCAAGCACTG  GGTGGTGATC
241 GTGGCAGGTT  CAAATGGCTG  GTATAATTAT  AGGCACCAGG
281 CAGACGCGTG  CCATGCCTAC  CAGATCATTC  ACCGCAATGG
321 GATTCCTGAC  GAACAGATCG  TTGTGATGAT  GTACGATGAC
361 ATTGCTTACT  CTGAAGACAA  TCCCACTGCA  GGAATTGTGA
401 TGAACAGGCC  CAATGGCACA  CATGTCTATC  AGGGAGTCCC
441 GAAGGACTAC  ACTGGAGAGG  ATGTTACCCG  ACAAAATTTC
481 CTTGCTGTGT  TGAGAGGCGA  TGCAGAAGCA  GTGAAGGGCA
521 TAGGATCCGG  CAAAGTCCTG  AAGAGTGGCC  CCCAGGATCA
561 CGTGTTCATT  TACTTCACTG  ACCATGGATC  TACTGGAATA
601 CTGGTTTTTC  CCAATGAAGA  TCTTCATGTA  AAGGAGGTGA
641 ATGAGACCAT  CCATTACATG  TACAAACACA  AAATGTACCG
681 AAAGATGGTG  TTCTACATTG  AAGCCTGTGA  GTCTGGGTCC
721 ATGATGAACC  ACCTGCCGGA  TAACATCAAT  GTTTATGCAA
761 CTACTGCTGC  CAACCCCAGA  GAGTCGTCCT  ACGCCTGTTA
801 CTATGATGAG  AAGAGGTCCA  CGTACCTGGG  GGACTGGTAC
841 AGCGTCAACT  GGATGGAAGA  CTCGGACGTG  GAAGATCTGA
881 CTAAAGAGAC  CCTGCACAAG  CAGTACCACC  TGGTAAAATC
921 GCACACCAAC  AGCAGCCACG  TCATGGAGTA  TGGAAACAAA
961 ACAATCTCCA  CCATGAAAGT  GATGCAGTTT  CAGGGTATGA
1001 AACGCAAAGC  CAGTTCTCCC  GTCCCCCTAC  CTCCAGTCAC
1041 ACACCTTGAC  CTCACCCCCA  GCCCTGATGT  GCCTCTCACC
1081 ATCATGAAAA  GGAAACTGAT  GAACACCAAT  GATCTGGAGG
1121 AGTCCAGGCA  GCTCACGGAG  GAGATCCAGC  GGCATCTGGA
1161 TGCCAGGCAC  CTCATTGAGA  AGTCAGTGCG  TAAGATCGTC
1201 TCCTTGCTGG  CAGCGTCCGA  GGCTGAGGTG  GAGCAGCTCC
1241 TGTCCGAGAG  AGCCCCGCTC  ACGGGGCACA  GCTGCTACCC
1281 AGAGGCCCTG  CTGCACTTCC  GGACCCACTG  CTTCAACTGG
1321 CACTCCCCCA  CGTACGAGTA  TGCGTTGAGA  CATTTGTACG
1361 TGCTGGTCAA  CCTTTGTGAG  AAGCCGTATC  CACTTCACAG
1401 GATAAAATTG  TCCATGGACC  ACGTGTGCCT  TGGTCACTAC
1441 TGAACAGCTG  CCTCCTGGAA  GCTTTTCCAA  GTGTGAGCGC
1481 CCCACCGACT  GTGTGCTGAT  CAGAGACTGG  AGAGGTGGAG
1521 TGAGAAGTCT  CGGCTGCTCG  GGCCCTCCTG  GGGAGCCCCC
1561 CCTCCAGGGC  TCGGTCGAGG  ACCTTCTTCA  CAAGATGACT
1601 TGCTCGCTGT  TACCTGCTTC  CCCAGTGTTT  TCTGAAAAAC
1641 TACAAATTAG  GGTGGGAAAA  GCTCTGTATT  GAGAAGGGTC
1681 ATATTTGCTT  TCTAGGAGGT  TTGTTGTTTT  GCCTGTTAGT
1721 TTTGAGGAGC  AGGAAGCTCA  TGGGGGCTTC  TGTAGCCCCT
1761 CTCAAAAGGA  GTCTTTATTC  TGAGAATTTG  AAGCTGAAAC
1801 CTCTTTAAAT  CTTCAGAATG  ATTTTATTGA  AGAGGGCCGC
1841 AAGCCCCAAA  TGGAAACTG   TTTTTAGAAA  ATATCATGAT
1881 TTTTGATTGC  TTTTGTATTT  AATTCTGCAG  GTGTTCAAGT
1921 CTTAAAAAAT  AAAGATTTAT  AACAGAACCC  AAAAAAAAA
1961 AAAAAAAAA  AAAAAAAAA  A
```

A genomic nucleotide sequence for human legumain can be found in the NCBI database at accession number NT 026437 (gi: 29736559). See website at ncbi.nlm.nih.gov. Naturally occurring allelic variants of legumain nucleic acids and proteins are also contemplated. An allelic variant is an alternate form of sequence which may have a substitution, deletion or addition at one or more positions, which does not substantially alter the function of the legumain.

Murine legumain shares about 83% sequence identity with the human protein (Barrett et al., 2001). An amino acid sequence for murine legumain can be found in the NCBI database at accession number O89017 (gi: 21617821).

Importantly, legumain has a highly restricted protease specificity. In particular, legumain cleaves polypeptide sequences on the N-terminal side of asparagine. Hence, legumain requires an asparagine at the P1 site of a substrate in order to cleave a protein or peptide.

Mammalian legumain has been implicated in processing of bacterial peptides and in processing endogenous proteins for MHC class II presentation in the lysosomal/endosomal systems (Manoury et al., 1998; Beck et al., 2001). Recently, human legumain has been identified as an inhibitor of osteoclast formation and has been associated with bone resorption (Choi et al., 2001). However, elucidation of legumain's functional role in molecular cell biology and pathobiology is limited, and association with tumor biology has not previously been demonstrated or suggested.

It is herein disclosed that cancerous tissues express legumain. Legumain expression is also correlated with a propensity for cell migration and cancer cell metastasis. In some embodiments, the legumain is expressed on the surface of the cancerous cells in which it is expressed.

The invention provides therapeutic and diagnostic compositions of prodrugs and other agents that can be targeted to tissues having cancerous cells. Some of the prodrugs and targeted agents of the invention contain a peptide that has an amino acid sequence that can be recognized, bound or cleaved by legumain. In other embodiments, the invention provides agents that can bind legumain, for example, legumain inhibitors and antibodies that recognize and bind legumain.

Legumain Prodrugs

In some embodiments of the invention, agents are designed to contain a drug compound that is activated following cleavage by legumain. These agents are referred to herein as legumain prodrugs.

Hence, the invention relates to a prodrug compound, including a drug molecule linked to a peptide, wherein the peptide has an amino acid sequence including two linked amino acids, wherein at least one of the two linked amino acids is Asn, and wherein legumain cleaves the peptide at the link between the two amino acids to generate an active drug from the prodrug. The term "drug" as used herein, refers to any medicinal substance used in humans or other animals. Encompassed within this definition are chemotherapeutic agents, cytotoxic agents, compound analogs, hormones, antimicrobials, neurotransmitters, etc. In some embodiments, the prodrugs of the invention include drug molecules whose activity is diminished when attached to peptide.

For example, in some embodiments the prodrug can have a structure similar to that provided for SEQ ID NO:3:

Pr-(Xaa1)$_n$-Xaa2-Asn-(Xaa3)-drug wherein:
Pr is a protecting group
n is an integer of about 0 to about 50;
Xaa1 and Xaa2 are separately any amino acid;
Xaa3 is either nothing or an amino acid that has no substantial effect on the activity of the drug; and
the drug employed is a drug whose action is diminished or blocked by attachment of a peptide to the drug.

In one embodiment, the invention provides legubicin as a prodrug of the invention that contains a cytotoxic agent, doxorubicin, linked to a peptidyl sequence (Boc-Ala-Ala-Asn-Leu, SEQ ID NO:4). The structure of legubicin is provided below as formula I.

Note that in legubicin, an amino group in doxorubicin is attached to the C-terminus of the peptide Boc-Ala-Ala-Asn-Leu (SEQ ID NO:4).

Intact legubicin is not significantly cytotoxic. However, legubicin becomes toxic after the amino acid sequence of the linked peptide (e.g., Boc-Ala-Ala-Asn-Leu (SEQ ID NO:4)) is cleaved by legumain. Legumain can cleave legubicin between the leucine and the asparagine of SEQ ID NO:4, thereby releasing doxorubicin-Leu to act as a cytotoxin on the cells that express legumain.

In general, while a peptide could be linked to the —CO—CH$_2$—OH moiety of doxorubicin to generate a prodrug having formula II, such a prodrug construct is less desirable than a doxorubicin prodrug having a linkage at the amino position shown in formula I. A less desirable doxorubicin prodrug having formula II is shown below.

While doxorubicin prodrugs having formula II can be properly targeted to legumain-expressing cells, such prodrugs appear to more toxic than prodrugs having linkages like those shown in formula I. Hence, linkage of peptides to the heterocyclic ring of doxorubicin is preferred.

As provided herein, peptides linked to drugs can have a variety of sequences and a variety of lengths to form the prodrugs of the invention. Hence, any peptide can be used so long as the peptide sequence contains Asn at a position sufficiently near the drug that the drug is active after cleavage of the prodrug. Generally, peptides are used that block or inhibit some or all of the drug's activity. In some embodiments, the linked peptide can have an amino acid sequence that includes the sequence Asn-Leu. In other embodiments, the peptide can have an amino acid sequence that includes the sequence Ala- Asn-Leu. Further embodiments can have peptides with an amino acid sequence that include the sequence Thr-Asn-Leu, or the sequence Ala-Ala-Asn-Leu (SEQ ID NO:5), or the sequence Ala-Thr-Asn-Leu (SEQ ID NO:6). In some embodiments, the peptide further can have an N-β-alanyl terminus, an N-terminal Boc or an N-terminal succinyl residue.

Specific examples of doxorubicin prodrugs contemplated by the invention include the following:

```
                                           (SEQ ID NO:7)
     Boc-Ala-Ala-Asn-Leu-doxorubicin.

(SEQ ID NO:8)
     Succinyl-Ala-Ala-Asn-Leu-doxorubicin.

(SEQ ID NO:9)
     Boc-Ala-Thr-Asn-Leu-doxorubicin.

(SEQ ID NO:10)
     Succinyl-Ala-Thr-Asn-Leu-doxorubicin.

(SEQ ID NO:11)
     Boc-Ala-Asn-Leu-doxorubicin.

(SEQ ID NO:12)
     Succinyl-Ala-Asn-Leu-doxorubicin.

(SEQ ID NO:13)
     Boc-Thr-Leu-doxorubicin.

(SEQ ID NO:14)
     Succinyl-Thr-Leu-doxorubicin.
```

In other embodiments of the invention, agents containing a detection agent are targeted to legumain-containing tissues for detection and diagnosis of cancer, cell migration or metastasis. Such diagnostic agents can include an agent that binds to legumain and a detectable label or reporter molecule. For example, such a diagnostic agent can be a legumain inhibitor or an anti-legumain antibody, that specifically recognizes or binds to legumain, and that has a label linked to it. These agents are useful for imaging, diagnosis, and for treating cancer and are discussed in more detail below.

In many embodiments, the agents and prodrugs of the invention are substantially non-immunogenic to the animal to which they are administered. The term "substantially non-immunogenic" means that the agent or prodrug can be administered to the animal on more than one occasion without causing a significant immune response. Such a significant immune response can be seen, for example, if a foreign protein or an antibody from another species were administered to the animal and a significant humoral or cellular immune response was initiated.

As described above, the prodrugs and diagnostic agents of the invention can include a peptide. For example, a peptide can be linked to a cytotoxic agent to modulate the cytotoxicity of the cytotoxic agent. In other embodiments, a peptide can be linked to a drug to modulate the activity of the drug. In other embodiments, a diagnostic agent can include a peptide that links a label or a reporter molecule to a an agent that binds to legumain. An agent that binds to legumain can be a peptide, for example, agents that bind to legumain include peptide substrates and peptide inhibitors of legumain. Other agents that bind to legumain include anti-legumain antibodies.

The peptides employed can have amino acid sequences comprised of any available amino acid, although in some embodiment the peptide has an asparagine residue at a desired cleavage site. Amino acids included in the peptides can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 1. These amino acids can be linked together, for example, by peptidyl linkages, intersubunit linkages, or other intersubunit linkages that are consistent with enzyme-substrate or receptor-ligand binding interactions.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| p-Aminophenylalanine | | Phe(pNH$_2$) |
| N-methylvaline | | MeVal |
| Homocysteine | | hCys |
| Homoserine | | hSer |
| ε-Amino hexanoic acid | | Aha |
| δ-Amino valeric acid | | Ava |
| 2,3-Diaminobutyric acid | | Dab |

Certain amino acids which are not genetically encoded and which can be present in agents of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(pNH$_2$), DBU, A$_2$ BU |
| Polar | Q, N, S, T, Y | Cit, AcLys, MSO, hSer |
| Cysteine-Like | C | Pen, hCys, β-methyl Cys |

Peptides described herein may be synthesized by methods available in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology,"Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection may be necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc. 85:2149, 1963, which involves assembling a linear peptide chain on a resin support using protected amino acids. Solid phase peptide synthesis typically utilizes either the Boc or Fmoc strategy, which are now well known in the art.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Drugs

According to the invention, any drug useful for modulating, treating or otherwise affecting the physiological state of a legumain-expressing cell can be attached to a legumain peptide substrate or an agent that can bind legumain. Agents that can bind legumain include legumain inhibitors, anti-legumain antibodies and the like. Attachment of drugs to legumain peptide substrates generates a prodrug of the invention. Similarly, attachment of a drug to an agent that can bind legumain permits delivery and accumulation of the drug in legumain-expressing cells.

While the invention is directed to attaching any drug to a legumain peptide substrate or an agent that can bind legumain, in some embodiments, the drug is a cytotoxic agent or an effector molecule. The cytotoxic agents and effector molecules useful in the practice of the invention include cytotoxins and chemotherapeutic agents. These agents include, but are not limited to, folate antagonists, pyrimidine antimetabolites, purine antimetabolites, alkylating agents, platinum antitumor agents, anthracyclines, DNA intercalators, epipodophyllotoxins, DNA topoisomerases, microtubule-targeting agents, vinca alkaloids, taxanes, epothilones and asparaginases. Further information can be found in Bast et al., CANCER MEDICINE, edition 5, which is available free as a digital book. See website at ncbi.nlm.nih.gov/books/bv.fcgi?call=bv View..ShowTOC&rid=cmed. TOC&depth=2.

Folic acid antagonists are cytotoxic drugs used as antineoplastic, antimicrobial, anti-inflammatory, and immune-suppressive agents. While several folate antagonists have been developed, and several are now in clinical trial, methotrexate (MTX) is the antifolate with the most extensive history and widest spectrum of use. MTX is an essential drug in the chemotherapy regimens used to treat patients with acute lymphoblastic leukemia, lymphoma, osteosarcoma, breast cancer, choriocarcinoma, and head and neck cancer, as well as being an important agent in the therapy of patients with non-malignant diseases, such as rheumatoid arthritis, psoriasis, and graft-versus-host disease.

Pyrimidine antimetabolites include fluorouracil, cytosine arabinoside, 5-azacytidine, and 2',2'-difluoro-2'-deoxycytidine. Purine antimetabolites include 6-mercatopurine, thioguanine, allopurinol (4-hydroxypyrazolo-3,4-d-pyrimidine), deoxycoformycin (pentostatin), 2-fluoroadenosine arabinoside (fludarabine; 9-β-d-arabinofuranosyl-2-fluoradenine), and 2-chlorodeoxyadenosine (Cl-dAdo, cladribine). In addition to purine and pyrimidine analogues, other agents have been developed that inhibit biosynthetic reactions leading to the ultimate nucleic acid precursors. These include phosphonacetyl-L-aspartic acid (PALA), brequinar, acivicin, and hydroxyurea.

Alkylating agents and the platinum anti-tumor compounds form strong chemical bonds with electron-rich atoms (nucleophiles), such as sulfur in proteins and nitrogen in DNA. Although these compounds react with many biologic molecules, the primary cytotoxic actions of both classes of agents appear to be the inhibition of DNA replication and cell division produced by their reactions with DNA. However, the chemical differences between these two classes of agents produce significant differences in their anti-tumor and toxic effects. The most frequently used alkylating agents are the nitrogen mustards. Although thousands of nitrogen mustards have been synthesized and tested, only five are commonly used in cancer therapy today. These are mechlorethamine (the original "nitrogen mustard"), cyclophosphamide, ifosfamide, melphalan, and chlorambucil. Closely related to the nitrogen mustards are the aziridines, which are represented in current therapy by thiotepa, mitomycin C, and diaziquone (AZQ). Thiotepa (triethylene thiophosphoramide) has been used in the treatment of carcinomas of the ovary and breast and for the intrathecal therapy of meningeal carcinomatosis. The alkyl alkane sulfonate, busulfan, was one of the earliest alkylating agents. This compound is one of the few currently used agents that clearly alkylate through an SN2 reaction. Hepsulfam, an alkyl sulfamate analogue of busulfan with a wider range of anti-tumor activity in preclinical studies, has been evaluated in clinical trials but thus far has demonstrated no superiority to busulfan. Busulfan has a most interesting, but poorly understood, selective toxicity for early myeloid precursors. This selective effect is probably responsible for its activity against chronic myelocytic leukemia (CML).

Topoisomerase poisons are believed to bind to DNA, the topoisomerase, or either molecule at or near the region of the enzyme involved in the formation of the DNA protein covalent linkage. Many topoisomerase poisons, such as the anthracyclines and actinomycin D, are relatively planar hydrophobic compounds that bind to DNA with high affinity by intercalation, which involves stacking of the compound between adjacent base pairs. Anthracyclines intercalate into double-stranded DNA and produce structural changes that interfere with DNA and RNA syntheses. Several of the clinically relevant anthracyclines are shown below.

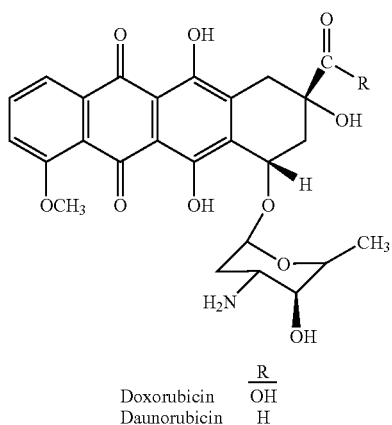

|  | R |
|---|---|
| Doxorubicin | OH |
| Daunorubicin | H |

-continued

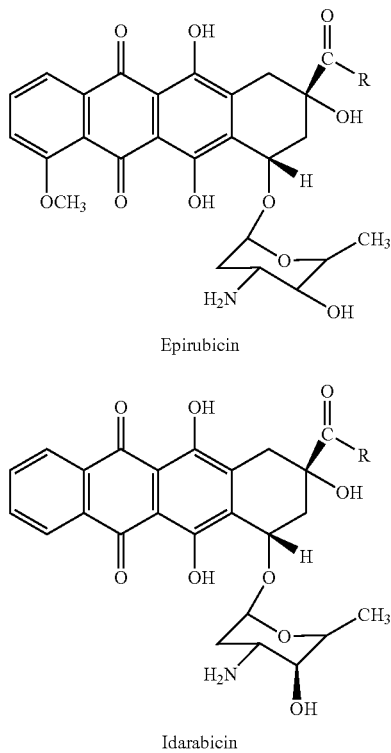

Epirubicin

Idarabicin

Non-intercalating topoisomerase-targeting drugs include epipodophyllotoxins such as etoposide and teniposide. Etoposide is approved in the United States for the treatment of testicular and small cell lung carcinomas. Etoposide phosphate is more water soluble than etoposide and is rapidly converted to etoposide in vivo. Other non-intercalating topoisomerase-targeting drugs include topotecan and irinotecan.

Unique classes of natural product anticancer drugs have been derived from plants. As distinct from those agents derived from bacterial and fungal sources, the plant products, represented by the Vinca and Colchicum alkaloids, as well as other plant-derived products such as paclitaxel (Taxol) and podophyllotoxin, do not target DNA. Rather, they either interact with intact microtubules, integral components of the cytoskeleton of the cell, or with their subunit molecules, the tubulins. Clinically useful plant products that target microtubules include the Vinca alkaloids, primarily vinblastine (VLB), vincristine (VCR), vinorelbine (Navelbine, VRLB), and a newer Vinca alkaloid, vinflunine (VFL; 20',20'-difluoro-3',4'-dihydrovinorelbine), as well as the two taxanes, paclitaxel and docetaxel (Taxotere).

Hence, examples of drugs that can be used to form prodrugs of the invention include, but are not limited to, Aldesleukin, Asparaginase, Bleomycin Sulfate, Camptothecin, Carboplatin, Carmustine, Cisplatin, Cladribine, Cyclophosphamide (lyophilized), Cyclophosphamide (non-lyophilized), Cytarabine (lyophilized powder), Dacarbazine, Dactinomycin, Daunorubicin, Diethylstilbestrol, Doxorubicin, Epoetin Alfa, Esperamycin, Etidronate, Etoposide, Filgrastim, Floxuridine, Fludarabine Phosphate, Fluorouracil, Goserelin, Granisetron Hydrochloride, Idarubicin, Ifosfamide, Immune Globulin, Interferon, Alpha-2a, Interferon Alpha-2b, Leucovorin Calcium, Leuprolide, Levamisole, Mechlorethamine, Medroxyprogesterone, Melphalan, Methotrexate, Mitomycin, Mitoxantrone, Octreotide, Ondansetron Hydrochloride, Paclitaxel, Pamidronate, Disodium, Pegaspargase, Plicamycin, Sargramostim, Streptozocin, Taxol, Thiotepa, Teniposide, Vinblastine, and Vincristine. Other toxic effector molecules for use in the present invention are disclosed, for example, in WO 98/13059; Payne, 2003; US 2002/0147138 and other references available to one of skill in the art.

Peptides can be conjugated to chemotherapeutic agents, drugs, reporter molecules, labels, cytotoxic agents and other entities by using peptidyl amino groups, carboxylate groups or side chain moieties of the peptidyl amino acids to form covalent linkages with such chemotherapeutic agents, drugs, reporter molecules, labels, cytotoxic agents and other agents. Amino acids can be conjugated to such entities by any method available to one of skill in the art. For example, functional groups present on the side chains of amino acids in the peptides can be combined with functional groups in the entity to which the peptide is conjugated. Functional groups that can form covalent bonds include, for example, —COOH and —OH; —COOH and —NH$_2$; and —COOH and —SH. Pairs of amino acids that can be used to conjugate proteins to the present peptides include, Asp and Lys; Glu and Lys; Asp and Arg; Glu and Arg; Asp and Ser; Glu and Ser; Asp and Thr; Glu and Thr; Asp and Cys; and Glu and Cys. Other examples of amino acid residues that are capable of forming covalent linkages with one another include cysteine-like amino acids such Cys, hCys, β-methyl-Cys and Pen, which can form disulfide bridges with one another. Other pairs of amino acids that can be used for conjugation and cyclization of the peptide will be apparent to those skilled in the art.

The groups used to conjugate a peptide to another agent need not be a side group on an amino acid. Examples of functional groups capable of forming a covalent linkage with the amino terminus of a peptide include, for example, carboxylic acids and esters. Examples of functional groups capable of forming a covalent linkage with the carboxyl terminus of a peptide include —OH, —SH, —NH$_2$ and —NHR where R is ($C_1$-$C_6$) alkyl, ($C_1$-$C_6$) alkenyl and ($C_1$-$C_6$) alkynyl.

The variety of reactions between two side chains with functional groups suitable for forming such linkages, as well as reaction conditions suitable for forming such linkages, will be apparent to those of skill in the art. Preferably, the reaction conditions used to conjugate the peptides to other entities are sufficiently mild so as not to degrade or otherwise damage the peptide. In particular, some embodiments require a functional legumain recognition site (e.g. an intact asparagine), so conditions should be adjusted to minimize damage to such sites. Suitable groups for protecting the various functionalities as necessary are well known in the art (see, e.g., Greene & Wuts, 1991, 2nd ed., John Wiley & Sons, NY), as are various reaction schemes for preparing such protected molecules.

Methods for linking peptides to other entities are available in the art. See Spatola, 1983, "Peptide Backbone Modifications" In: Chemistry and Biochemistry of Amino Acids Peptides and Proteins (Weinstein, ed.), Marcel Dekker, New York, p. 267 (general review); Morley, 1980, Trends Pharm. Sci. 1:463-468; Hudson et al., 1979, Int. J. Prot. Res. 14:177-185 (—CH$_2$NH—, —CH$_2$CH$_2$—); Spatola et al., 1986, Life Sci. 38:1243-1249 (—CH$_2$—S); Hann, 1982, J. Chem. Soc. Perkin Trans. I. 1:307-314 (—CH=CH—, cis and trans); Almquist et al., 1980, J. Med. Chem. 23:1392-1398 (—CO CH$_2$—); Jennings-White et al., Tetrahedron. Lett. 23:2533 (—CO CH$_2$—); European Patent Application EP 45665 (1982) CA:97:39405 (—CH(OH)CH$_2$—); Holladay et al., 1983, Tetrahedron Lett. 24:4401-4404 (—C(OH)CH$_2$—); and Hruby, 1982, Life Sci. 31:189-199 (—CH$_2$—S—).

Cancer Treatment

In certain aspects of the inventions, the prodrug compounds and agents described herein are useful for preventing, treating or diagnosing cancer. As used herein, the term "cancer" includes solid mammalian tumors as well as hematological malignancies.

"Solid mammalian tumors" include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin.

The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS.

In addition, a cancer at any stage of progression can be treated, such as primary, metastatic, and recurrent cancers. The invention can also be used to treat autoimmune deficiency syndrome-associated Kaposi's sarcoma, cancer of the adrenal cortex, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries. A cancer at any stage of progression can be treated or detected, such as primary, metastatic, and recurrent cancers. Information regarding numerous types of cancer can be found, e.g., from the American Cancer Society (www.cancer.org), or from, e.g., Wilson et al. (1991) Harrison's Principles of Internal Medicine, 12th Edition, McGraw-Hill, Inc. Both human and veterinary uses are contemplated.

As used herein the terms "normal mammalian cell" and "normal animal cell" are defined as a cell that is growing under normal growth control mechanisms (e.g., genetic control) and that displays normal cellular differentiation and normal migration patterns. Cancer cells differ from normal cells in their growth patterns, migration and in the nature of their cell surfaces. For example cancer cells tend to grow continuously and chaotically, without regard for their neighbors, and can sometimes migrate to distal sites to generate tumors in other areas of the body.

The present invention is directed, in some embodiments, to methods of treating cancer in an animal, for example, for human and veterinary uses, which include administering to a subject animal (e.g., a human), a therapeutically effective amount of an agent (e.g. a prodrug or a legumain inhibitor) of the present invention.

Treatment of, or treating, cancer is intended to include the alleviation of or diminishment of at least one symptom typically associated with the disease. The treatment also includes alleviation or diminishment of more than one symptom. The treatment may cure the cancer, e.g., it may substantially kill the cancer cells and/or it may arrest or inhibit the growth of the cancerous tumor.

Anti-cancer activity can be evaluated against varieties of cancers using methods available to one of skill in the art. Anti-cancer activity, for example, is determined by identifying the lethal dose (LD100) or the 50% effective dose (ED50) or the dose that inhibits growth at 50% (GI50) of an agent of the present invention that prevents the growth of a cancer. In one aspect, anti-cancer activity is the amount of the agents that kills 50% or 100% of the cancer cells, for example, when measured using standard dose response methods.

The present invention also provides a method of evaluating a therapeutically effective dosage for treating a cancer with an agent of the invention that includes determining the LD100 or ED50 of the agent in vitro. Such a method permits calculation of the approximate amount of agent needed per volume to inhibit cancer cell growth or to kill 50% to 100% of the cancer cells. Such amounts can be determined, for example, by standard microdilution methods.

In some embodiments, the agents of the invention can be administered in multiple doses over a period of one to seven days.

The term "animal," as used herein, refers to an animal, such as a warm-blooded animal, which is susceptible to or has a disease associated with legumain expression, for example, cancer. Mammals include cattle, buffalo, sheep, goats, pigs, horses, dogs, cats, rats, rabbits, mice, and humans. Also included are other livestock, domesticated animals and captive animals. The term "farm animals" includes chickens, turkeys, fish, and other farmed animals. Mammals and other animals including birds may be treated by the methods and compositions described and claimed herein.

Other Therapeutic Methods

In addition to expression in cancer cells, legumain is expressed in monocytes. Such monocyte expression is differentially regulated by GM-CSF and M-CSF. Legumain may also be involved in monocyte or macrophage migration or infiltration, and in antigen processing. Recently, legumain, has been identified as an inhibitor of osteoclast formation and is associated with bone resorption. Choi, S. J., et al., *Osteoclast inhibitory peptide 2 inhibits osteoclast formation via its C-terminal fragment.* J Bone Miner Res, 2001. 16(10): p. 1804-11.

Accordingly, the invention also contemplates inhibiting osteoclast activity, for example, to prevent and treat osteoporosis. Methods for inhibiting osteoclast activity or for preventing or treating osteoporosis in an animal involve administering to the animal an agent that inhibits legumain. Any inhibitor of legumain can be utilized, for example, any of the inhibitors described herein.

As described herein, legumain is expressed in monocytes. Monocytes and macrophage originate from multipotential progenitor cells in bone marrow and play a pivotal role in host defense to pathogens, wound healing, angiogenesis, and various types of chronic inflammatory responses. Under chemokine and other cytokine induction monocytes migrate to tissues and differentiate into macrophages. Macrophages in various tissue and disease states vary in their morphology and function and have been given different names, e.g. Kupffer cells in liver, microglial cells in the central nervous system, and foam cells in atherosclerotic lesions. GM-CSF and M-CSF independently induce proliferation and differentiation of monocytes into distinct subsets of macrophages. Legumain is not detectable in freshly isolated unstimulated monocytes, but is up-regulated by both GM-CSF and M-CSF. Hashimoto, S., et al., *Serial analysis of gene expression in human monocytes and macrophages.* Blood, 1999. 94(3): p. 837-44. M-CSF induced macrophages express a greater amount of legumain than GM-CSF induced macrophages.

According to the invention, legumain can influence monocyte/macrophage migration, infiltration, and antigen processing. M-CSF is a potent chemoattractant for cells of monocytes and macrophage lineages. Wang, J. M., et al., *Induction of monocyte migration by recombinant macrophage colony-stimulating factor.* J Immunol, 1988. 141(2): p. 575-9. GM-CSF lacks chemotactic and chemokinetic effects, but enhances monocyte transendothelial migration in response to C5a or monocyte chemoattractant protein-1. Shang, X. Z. and A. C. Issekutz, *Enhancement of monocyte transendothelial migration by granulocyte-macrophage colony-stimulating factor: requirement for chemoattractant and CD11a/CD18 mechanisms.* Eur J Immunol, 1999. 29(11): p. 3571-82. Hence, legumain expression may be involved in increasing or modulating the migratory and infiltration activities of monocytes and/or macrophages.

The invention provides a method for modulating the migration and/or infiltration of cells that includes contacting the cells with legumain or an inhibitor of legumain. In general, increased levels of legumain can stimulate cellular migration and/or infiltration whereas inhibition of legumain can decrease cellular migration and/or infiltration. Such methods may be used in vitro or in vivo. Such methods may be useful not only for treating and preventing cancer but for treating and preventing inflammatory diseases, autoimmune diseases and atherosclerosis.

Imaging and Detection

In one embodiment, the agents and methods provided herein can be used to diagnose the location, extent, and pathologic composition of cancer anywhere within the body of a mammal. For example, detection of an agent capable of binding to or becoming activated by legumain can provide information regarding the location, shape, extent and pattern of the cancer. A reporter molecule, label or signaling compound can be attached to agents and inhibitors that can bind to, or be activated by, legumain. Such conjugates can then be used in vivo or in vitro to image, locate or otherwise detect the tissue to which the agent binds.

The reporter molecule, label or signaling compound that is linked to the agent or inhibitor will, of course, depend on the ultimate application of the invention. Where the aim is to provide an image of the tumor, one of skill in the art may desire to use a diagnostic agent that is detectable upon imaging, such as a paramagnetic, radioactive or fluorogenic agent. Such agents are available in the art, for example, as described and disclosed in U.S. Pat. No. 6,051,230 which is incorporated by reference herein in its entirety. Many diagnostic agents are known in the art to be useful for imaging purposes, as are methods for their attachment to peptides and antibodies (see, e.g., U.S. Pat. Nos. 5,021,236 and 4,472,509, both incorporated herein by reference).

In the case of paramagnetic ions, one of skill may choose to use, for example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being preferred. Ions useful in other contexts, such as X-ray imaging, include but are not limited to lanthanum (III), gold (III), lead (II), and especially bismuth (III). Moreover, in the case of radioactive isotopes for therapeutic and/or diagnostic application, one might mention iodine$^{131}$, iodine$^{123}$, iodine$^{125}$, technicium$^{99}$, indium$^{111}$, phosphorus$^{32}$, rhenium$^{188}$, rhenium$^{186}$, gallium$^{67}$, sulfur$^{35}$, copper$^{67}$, yttrium$^{90}$, tritium$^{3}$ or astatine$^{211}$.

In some embodiments, agents and inhibitors may be conjugated with a dye or fluorescent moiety or intermediate such as biotin. Such conjugates can, for example, be used with infrared spectroscopy to detect and locate the tissues to which the agents bind.

In general, an assay for identifying legumain involves incubating a test sample under conditions that permit binding of legumain to a diagnostic agent, and measuring whether such binding has occurred. In some embodiments, the extent of binding between the diagnostic agent and legumain may be detected. Such information may be used to detect and assess the extent, spread or size of a cancerous tumor. A reporter molecule can be attached to any molecule that stably binds to legumain and that can be detected. For example, the reporter molecule can be attached to a legumain inhibitor or an anti-legumain antibody that is labeled as described above with paramagnetic ions, ions, radioactive isotopes, fluorescent dyes (e.g., fluorescein, rhodamine), enzymes and the like. It is understood that the choice of a reporter molecule will depend upon the detection system used.

Legumain Inhibitors

The present invention also provides a method of inhibiting cancer cell growth or tumor progression or tumor metastasis or invasion, for example, by inhibiting the expression or enzymatic activity of legumain. According to the invention, legumain may be inhibited by any available mechanism, including by use of a legumain inhibitor, a cysteine protease inhibitor or by inhibition of legumain transcription or translation. In another embodiment, a legumain inhibitor may be used to deliver a drug to a legumain-expressing cell. When a legumain inhibitor is used to deliver a drug to a legumain-expressing cell, the legumain inhibitor preferably does not substantially block or inhibit the activity of the drug.

In some embodiments, the invention provides antagonists or agonists for legumain. Such antagonists or agonists may be inhibitors or co-factors of legumain, including proteins, peptides, carbohydrates, lipids or small molecular weight molecules, which interact with legumain to regulate or modulate its activity. Other molecules contemplated as agents for modulating legumain include antibodies targeted against legumain as well as molecules, compounds or peptides that mimic legumain substrates or inhibitors in structure and that bind to and form inactive complexes with legumain. Potential polypeptide antagonists include antibodies that react with legumain.

Legumain and other cysteine protease inhibitors are available in the art. See, e.g. Asgian, J. L., et al., *Aza-peptide epoxides: a new class of inhibitors selective for clan CD cysteine proteases*. J Med Chem, 2002. 45(23): p. 4958-60; Niestroj, A. J., et al., *Inhibition of mammalian legumain by michael acceptors and AzaAsn-halomethylketones*. Biol Chem, 2002. 383(7-8): p. 1205-14; and U.S. Pat. No. 6,004,933, which are incorporated herein by reference. The invention contemplates using any such inhibitors as blocking or delivery agent in legumain-expressing cells.

In some embodiments, the legumain inhibitor is an inhibitor including formula III or IV:

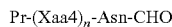    III

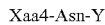    IV wherein:

Pr is a protecting group;

n is an integer of about 2 to about 5;

Xaa4 is an amino acid or an amino acid mimetic;

Y is alkyl or alkenyl, optionally substituted with 1-3 halo or hydroxy, alkylamino, dialkylamino, alkyldialkylamino, or cycloalkyl, alkylcycloalkyl, alkenylcycloalkyl, aryl; $(C_5-C_{12})$arylalkyl or $(C_5-C_{12})$arylalkenyl, wherein the aryl groups of the arylalky or arylalkenyl can be 0-4 heteroatoms selected from N, O and S, and are optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, $(C_5-C_6)$aryl, —O—$(C_5-C_6)$aryl, arylcarboxamide, alkylthio or haloalkylthio; and wherein the inhibitor is capable of binding to legumain.

Legumain inhibitors that can be used include legumain catalytic inhibitors, such as cystatin, stefin, Tissue Inhibitor of Metalloproteinase 2 (TIMP-2) and a peptide having the sequence Ala-Leu-β-Asn-Ala-Ala (SEQ ID NO:15).

The Ala-Leu-β-Asn-Ala-Ala (SEQ ID NO:15) peptide is a synthetic suicide inhibitor that is useful as a legumain inhibitor, where the beta linkage is present to prevent hydrolysis. The SEQ ID NO:15 peptide will then remain bound to the legubicin catalytic site and block its activity.

In other embodiments, the invention provides anti-sense RNA or DNA molecules to modulate legumain expression, legumain translation and/or the degradation of legumain transcripts. For example, an anti-sense RNA or DNA that can hybridize to a legumain nucleic acid can be used as an anti-sense RNA or DNA for diminishing the expression of legumain. The legumain nucleic acid can have SEQ ID NO:2 or can have a sequence related to a genomic nucleotide sequence for human legumain that can be found in the NCBI database at accession number NT 026437 (gi: 29736559). See website at ncbi.nlm.nih.gov.

The degradation of legumain mRNA may also be increased upon exposure to small duplexes of synthetic double-stranded RNA through the use of RNA interference (siRNA or RNAi) technology. Scherr, M et al. Curr Med Chem 2003 10:245; Martinez, L A et al. 2002 PNAS 99: 14849. A process is therefore provided for inhibiting expression of legumain in a cell. The process includes introduction of RNA with partial or fully double-stranded character into the cell or into the extracellular environment. Inhibition is specific to legumain RNA because a nucleotide sequence from a portion of the legumain gene is chosen to produce inhibitory RNA. This process is effective in producing inhibition of gene expression.

The pSuppressorNeo vector for expressing hairpin siRNA, commercially available from IMGENEX (San Diego, Calif.), can be used to generate siRNA for inhibiting legumain expression. The most critical part of the construction of the siRNA expression plasmid is the selection of the target region of the mRNA, which is currently a trial-and-error process. However, Elbashir et al. have provided guidelines that appear to work ~80% of the time. Elbashir, S. M., et al., *Analysis of gene function in somatic mammalian cells using small interfering RNAs*. Methods, 2002. 26(2): p. 199-213. Accordingly for synthesis of synthetic siRNA, a target region may be selected preferably 50 to 100 nucleotides downstream of the start codon. The 5' and 3' untranslated regions and regions close to the start codon should be avoided as these may be richer in regulatory protein binding sites. The ideal sequence for a synthetic siRNA is 5'-AA(N19)UU, where N is any nucleotide in the mRNA sequence and should be approximately 50% G-C content. The selected sequence(s) can be compared to others in the human genome database to minimize homology to other known coding sequences (Blast search, for example, through the NCBI website).

However, for designing oligonucleotides for the expression vector, AA and UU dimers in the sequence are not needed. For the expression vector, siRNA can be designed to produce hairpin RNAs, in which both strands of an siRNA duplex would be included within a single RNA molecule. The individual motif can be 19-21 nucleotides long and correspond to the coding region of the legumain gene. However, Paddison and Hannon, 2002 have suggested use of 18-28 nucleotides. Paddison, P. J. and G. J. Hannon, *RNA interference: the new somatic cell genetics?* Cancer Cell, 2002. 2(1): p. 17-23; Paddison, P. J., et al., *Short hairpin RNAs (shRNAs)* induce sequence-specific silencing in mammalian cells. Genes Dev, 2002. 16(8): p. 948-58. The two motifs that form the inverted repeat are separated by a spacer of 4-9 nucleotides to permit formation of a hairpin loop. The transcriptional termination signal for 5 T's is added at the 3' end of the inverted repeat.

The siRNA insert can be prepared by synthesizing and annealing of two complementary oligonucleotides, and directly ligated this insert into the vector DNA. The resultant legumain suppressing vector DNA can be used to generate cell line that stably incorporates this vector and selection for retention of the construct can be achieved by selection of a linked marker. Such cell line is useful for preparing siRNA molecules for use in inhibiting legumain.

Mixtures and combinations of such siRNA molecules are also contemplated by the invention. These compositions can be used in the methods of the invention, for example, for treating or preventing cancer or metastasis. These compositions are also useful for modulating (e.g. decreasing) legumain expression.

The siRNA provided herein can selectively hybridize to RNA in vivo or in vitro. A nucleic acid sequence is considered to be "selectively hybridizable" to a reference nucleic acid sequence if the two sequences specifically hybridize to one another under physiological conditions or under moderate stringency hybridization and wash conditions. In some embodiments the siRNA is selectively hybridizable to an RNA (e.g. a legumain RNA) under physiological conditions. Hybridization under physiological conditions can be measured as a practical matter by observing interference with the function of the RNA. Alternatively, hybridization under physiological conditions can be detected in vitro by testing for siRNA hybridization using the temperature (e.g. 37° C.) and salt conditions that exist in vivo.

Moreover, as an initial matter, other in vitro hybridization conditions can be utilized to characterize siRNA interactions. Exemplary in vitro conditions include hybridization conducted as described in the Bio-Rad Labs ZetaProbe manual (Bio-Rad Labs, Hercules, Calif.); Sambrook et al., *Molecular Cloning: A Laboratory Manual,* 2nd ed., Cold Spring Harbor Laboratory Press, (1989), or Sambrook et al., *Molecular Cloning: A Laboratory Manual,* 3rd ed., Cold Spring Harbor Laboratory Press, (2001)), expressly incorporated by reference herein. For example, hybridization can be conducted in 1 mM EDTA, 0.25 M $Na_2 HPO_4$ and 7% SDS at 42° C., followed by washing at 42° C. in 1 mM EDTA, 40 mM $NaPO_4$, 5% SDS, and 1 mM EDTA, 40 mM $NaPO_4$, 1% SDS. Hybridization can also be conducted in 1 mM EDTA, 0.25 M $Na_2 HPO_4$ and 7% SDS at 60° C., followed by washing in 1 mM EDTA, 40 mM $NaPO_4$, 5% SDS, and 1 mM EDTA, 40 mM $NaPO_4$, 1% SDS. Washing can also be conducted at other temperatures, including temperatures ranging from 37° C. to at 65° C., from 42° C. to at 65° C., from 37° C. to at 60° C., from 50° C. to at 65° C., from 37° C. to at 55° C., and other such temperatures.

The siRNA employed in the compositions and methods of the invention may be synthesized either in vivo or in vitro. In some embodiments, the siRNA molecules are synthesized in vitro using methods, reagents and synthesizer equipment available to one of skill in the art. Endogenous RNA polymerases within a cell may mediate transcription in vivo, or cloned RNA polymerase can be used for transcription in vivo or in vitro. For transcription from a transgene or an expression construct in vivo, a regulatory region may be used to transcribe the siRNA strands.

Depending on the particular sequence utilized and the dose of double stranded siRNA material delivered, the compositions and methods may provide partial or complete loss of function for the target gene (legumain). A reduction or loss of gene expression in at least 99% of targeted cells has been shown for other genes. See, e.g., U.S. Pat. No. 6,506,559. Lower doses of injected material and longer times after administration of the selected siRNA may result in inhibition in a smaller fraction of cells.

The siRNA may comprise one or more strands of polymerized ribonucleotide; it may include modifications to either the phosphate-sugar backbone or the nucleoside. The double-stranded siRNA structure may be formed by a single self-complementary RNA strand or two complementary RNA strands. siRNA duplex formation may be initiated either inside or outside the cell. The siRNA may be introduced in an amount that allows delivery of at least one copy per cell. Higher doses of double-stranded material may yield more effective inhibition.

Inhibition is sequence-specific in that nucleotide sequences corresponding to the duplex region of the RNA are targeted for genetic inhibition. siRNA containing nucleotide sequences identical to a portion of the target gene is preferred for inhibition. However, siRNA sequences with insertions, deletions, and single point mutations relative to the target sequence have also been found to be effective for inhibition. Thus, sequence identity may optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

The siRNA may be directly introduced into the cell (i.e., intracellularly); or introduced extracellularly into a cavity, interstitial space, into the circulation of an organism, introduced orally, or may be introduced by bathing an organism in a solution containing siRNA. Methods for oral introduction include direct mixing of siRNA with food of the organism, as well as engineered approaches in which a species that is used as food is engineered to express an siRNA, then fed to the organism to be affected. Physical methods of introducing nucleic acids include injection directly into the cell or extracellular injection into the organism of an siRNA solution.

The siRNA may also be delivered in vitro to cultured cells using transfection agents available in the art such as lipofectamine or by employing viral delivery vectors such as those from lentiviruses. Such in vitro delivery can be performed for testing purposes or for therapeutic purposes. For example, cells from a patient can be treated in vitro and then re-administered to the patient.

The advantages of using siRNA include: the ease of introducing double-stranded siRNA into cells, the low concentration of siRNA that can be used, the stability of double-stranded siRNA, and the effectiveness of the inhibition. The ability to use a low concentration of a naturally-occurring nucleic acid avoids several disadvantages of anti-sense interference.

Anti-Legumain Antibodies

The invention provides antibody preparations directed against legumain, for example, antibodies capable of binding a polypeptide having SEQ ID NO:1.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha ($\alpha$), delta ($\delta$), epsilon ($\epsilon$), gamma ($\gamma$) and mu ($\mu$), respectively. The light chains of antibodies can be assigned to one of two clearly distinct types, called kappa ($\kappa$) and lambda ($\lambda$), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a $\beta$-sheet configuration, connected by three CDRs, which form loops connecting, and in some cases forming part of, the $\beta$-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR) and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments contemplated by the invention are therefore not full-length antibodies but do have similar or improved immunological properties relative to an anti-legumain antibody. Such antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it binds with specificity to legumain, e.g. a polypeptide having SEQ ID NO:1.

Antibody fragments retain some ability to selectively bind with its antigen. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv including only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further includes a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

Methods for preparing polyclonal antibodies are available to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

Methods for preparing monoclonal antibodies are likewise available to one of skill in the art. See, for example, Kohler & Milstein, Nature, 256:495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Methods of in vitro and in vivo manipulation of monoclonal antibodies are also available to those skilled in the art. For example, monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol. Biol. 222: 581-597 (1991). Another method involves humanizing a monoclonal antibody by recombinant means to generate antibodies containing human specific and recognizable sequences. See, for review, Holmes, et al., J. Immunol., 158:2192-2201 (1997) and Vaswani, et al., Annals Allergy, Asthma & Immunol., 81:105-115 (1998).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates that the antibody preparation is a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad. Sci. 81, 6851-6855 (1984).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be non-covalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946, 778; and Pack, et al., *Bio/Technology* 11:1271-77 (1993).

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Immunol., 81:105-115 (1998).

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody. One method of mutating antibodies involves affinity maturation using phage display.

The invention is therefore directed to a method for selecting antibodies and/or antibody fragments or antibody polypeptides with desirable properties. Such desirable properties can include increased binding affinity or selectivity for the epitopes of the invention The antibodies and antibody fragments of the invention are isolated antibodies and antibody fragments. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or nonproteinaceous solutes. The term "isolated antibody" also includes antibodies within recombinant cells because at least one component of the antibody's natural environment will not be present. Ordinarily, however, isolated antibody will be prepared by at least one purification step If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In some embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain.

Methods of Detecting and Isolating Agents that can Modulate Legumain

The invention further provides screening assays that are useful for generating or identifying therapeutic agents for prevention and treatment of cancer and assays for generating or identifying agents that modulate legumain activity. In particular, the legumain substrates, legumain inhibitors, legumain nucleic acids and legumain proteins identified herein may be used in a variety of assays for detecting legumain and for identifying factors that interact with legumain nucleic acids or with the legumain protein. For example, in some embodiments, assays can be performed to assess whether a potential prodrug can be activated by legumain cleavage.

Prodrug conversion assay may be carried out in a variety of ways. For example, a cytotoxic agent can be linked to a peptide that has a legumain cleavage site as described above. Cultured non-cancerous cells and cancerous cells (e.g., those that express legumain) may then be separately exposed to the prodrug. After a suitable exposure time, the cultures are observed to ascertain whether the cancerous cells are preferentially killed or inhibited in their growth. The culture fluids may also be assayed to determine whether the prodrug has been cleaved in a manner that is consistent with legumain cleavage. Before such assays are performed, prodrug candidates can be screened to ascertain whether they are efficiently cleaved by legumain. In some embodiments, the cancer cells employed overexpress legumain.

Further assays can be performed to assess the in vivo toxicity and in vivo efficacy for treating cancer. Suitable animal models and tumor cell lines can be used for these purposes. For example, mice, rats or other model animals with a propensity for developing cancer can be employed. Alternatively, small tumors or tumor cells or cancer cells that overexpress legumain can be transplanted into normal animals. Some of the animals that received tumors, tumor cells or legumain+ cells are then treated with the prodrug. Other of those animals can be treated with the cytotoxic agent that forms part of the prodrug. Tumor growth and physical signs can be monitored daily including any gross evidence of tumor necrosis, local tumor ulceration as well as evidence of toxicity including mobility, response to stimulus, eating, and weight of each animal. Prodrugs that effectively reduce or eliminate tumors while having minimal negative effects on the health, lifespan and tissue integrity of the model animal are selected for development as a prodrug.

Assays may be used to identify agents that can interact with a cancer cell of interest. A wide variety of assays may be used for this purpose. See, for example, the assays carried out within the National Cancer Institute's "In Vitro Cell Line Screening Project." In general, such an assay can involve contacting a cancer cell of interest with at least one agent and observing whether the agent kills the cancer cell and/or has other deleterious effects upon that cell.

Methods available in the art can also be used for determining whether the agents of the invention interact with the membrane of a cancer cell of interest. For example, the agent can be labeled with a reporter molecule that permits detection of the agent. After labeling, the agents can be contacted with the cancer cell of interest for a time and under conditions that permit binding or association of the agent to cellular membranes. The cells can be washed with physiological solutions to remove unbound or unassociated agents, and the cells can then be observed to ascertain whether the reporter molecule is bound or associated with the cells or the cellular membranes. In another embodiment, one of skill in the art can test whether the agent(s) can penetrate the membranes of selected cancer cells. This may be done by examining whether the reporter molecule remains associated with the cellular membranes of the cancer cell or whether the reporter molecule becomes associated with the interior of the cell.

Reporter molecules that can be employed include any detectable compound or molecule that is conjugated directly or indirectly to an agent of the invention. The label may itself be detectable (e.g., radioisotope labels or fluorescent labels) or, in the case of an enzymatic label, may catalyze chemical alteration of a substrate compound or composition that is detectable.

Deleterious effects upon the cancer cell of interest can also be detected as an indication of an interaction between an agent of the invention and the cell. Such deleterious effects can involve any evidence that the agent has had an adverse or cytotoxic effect upon the cell. For example, one of skill in the art can test whether the agent(s) kill the cancer cell, cause membrane depolarization, cause permeabilization of the membranes of the cell, or tend to lyse the cancer cells.

Pluralities of assays can be performed in parallel with different agents at different concentrations to obtain a differential response to the various concentrations. Typically, at least one control assay is included in the testing. Such a control can be a negative control involving exposure of the cancer cells of interest to a physiologic solution containing no agents. Another control can involve exposure of the cancer cell of interest to an agent that has already been observed to adversely affect the cancer cell of interest, or a second cell that is related to the cell of interest. Another control can involve exposing a cell of interest to a known therapeutic compound that has a desired affect on the cancer cell of interest, for example, an anti-cancer agent with known efficacy at a particular concentration or dosage. One of skill in the art can readily select control compounds and conditions that facilitate screening and analysis of the effects of the cyclic peptides on a cancer cell of interest.

Any cell type can be assayed by these methods. For example, any mammalian or other animal cancer cell type can be screened to assess whether the agents of the invention can selectively interact therewith. Mammalian or other animal cells can also be screened to ascertain whether the agents of the invention selectively interact therewith and/or to determine whether the agents of the invention do not interact, bind, lyse, kill or otherwise adversely affect the viability of the mammalian or other animal cell.

Conditions for screening include conditions that are used by one of skill in the art to grow, maintain or otherwise culture cell types of interest. Cancer cell types of interest should be assayed under conditions where they would be healthy but for the presence of the agents. Controls can be performed where the cell types are maintained under the selected culture conditions and not exposed to an agent, to assess whether the culture conditions influenced the viability of the cells. One of skill in the art can also perform the assay on cells that have been washed in simple physiological solutions, such as buffered saline, to eliminate, or test for, any interaction between the agents or cells and the components in the culture media. However, culture conditions for the assays generally include providing the cells with the appropriate concentration of nutrients, physiological salts, buffers and other components typically used to culture or maintain cells of the selected type. A variety of other reagents may be included in the screening assay. These include reagents like salts, neutral proteins, albumin, and serum (e.g. fetal calf serum) that are used to mimic the physiologic state of the cell types of interest. Conditions and media for culturing, growing and maintaining cells are available to one of skill in the art.

The selected reagents and components are added to the assay in the order selected by one of skill in the art. In general, the agents are added last to start the assay. Assays are performed at any suitable temperature, typically between 4° C. and 40° C. For example, the temperature may generally range from about room temperature (about 20° C.) to about 37° C. Incubation periods are selected to ascertain the optimal range of activity, or to insure that the agents do not adversely affect the cell type of interest. However, incubation times can be optimized to facilitate rapid high-throughput screening. Typically, incubation times are between about one minute and about five days, such as a range from about 30 minutes to about 3 days.

Agents having the desired activity in vitro may be tested for activity and/or lack of toxicity in vivo, in an appropriate animal model. Such animal models include primates as well as mice, rats, rabbits, cats, dogs, pigs, goats, cattle or horses. For example, the mouse is a convenient animal model for testing whether agents of the invention have toxic effects and/or to determine whether the agents can inhibit the growth of a cancer cell.

One of skill in the art can readily perform in vivo evaluation of the agents of the invention. For toxicity testing, a series of agents at different test dosages can be separately administered to different animals. A single dose or, a series of dosages can be administered to the animal. A test period is selected that permits assessment of the effects of the agent(s) on the animal. Such a test period can run from about one day to about several weeks or months.

The effect of a agent(s) on an animal can be determined by observing whether the agent adversely affects the behavior (e.g., lethargy, hyperactivity) and physiological state of the animal over the course of test period. The physiological state of the animal can be assessed by standard procedures. For example, during the test period one of skill in the art can draw blood and collect other bodily fluids to test, for example, for various enzymes, proteins, metabolites, and the like. One of skill in the art can also observe whether the animal has bloating, loss of appetite, diarrhea, vomiting, blood in the urine, loss of consciousness, and a variety of other physiological problems. After the test period, the animal can be sacrificed and anatomical, pathological, histological and other studies can be performed on the tissues or organs of the animal.

In general, to determine whether one or more agents of the invention can inhibit cancer cell growth, mice are infected with the selected cancer and a selected test dosage of one or more agents is administered shortly thereafter. Mice are observed over the course of several days to several weeks to ascertain whether the agents protect the mice from the cancer. At the end of the test period, mice can be sacrificed and examined to ascertain whether the agent has optimally protected the mice from cancer and/or to determine whether any adverse side effects have occurred.

Controls are used to establish the effects of the cancer when the agent is not administered. Other controls can also be performed, for example, to determine the safety and efficacy of the present agents compared to that of known anti-cancer compounds.

Binding assays between legumain and other agents may be carried out in several formats, including cell-based binding assays, solution-phase assays and immunoassays. In general, test samples or compounds are incubated with legumain for a specified period of time followed by measurement of binding between legumain and the test sample or compound. A label or reporter molecule attached to the legumain, test sample or compound may be detected by use of microscopy, fluorimetry, a scintillation counter, or any available immunoassay. Binding can also be detected by labeling legumain in a competitive radioimmunoassay. Alternatively, legumain may be modified with an unlabeled epitope tag (e.g., biotin, peptides, $His_6$, FLAG, myc etc.) and bound to proteins such as streptavidin, anti-peptide or anti-protein antibodies that have a detectable label as described above. Additional forms of legumain containing epitope tags may be used in solution and immunoassays.

Methods for identifying compounds or molecules that interact with legumain are also encompassed by the invention. In general, an assay for identifying compounds or molecules that interact with legumain involves incubating legumain with a test sample that may contain such a compound or molecule under conditions that permit binding of the compound or molecule to legumain, and measuring whether binding has occurred. Legumain may be purified or present in mixtures, such as in cultured cells, tissue samples, body fluids or culture medium. Assays may be developed that are qualitative or quantitative. Quantitative assays can be used for determining the binding parameters (affinity constants and kinetics) of the compound or molecule for legumain and for quantifying levels of biologically active compounds and molecules in mixtures. Assays may also be used to evaluate the binding of a compound or molecule to fragments, analogs and derivatives of legumain and to identify new legumain family members.

The compound or molecule in a test sample may be substantially purified or present in a crude mixture. Binding compounds and molecules may be nucleic acids, proteins, peptides, carbohydrates, lipids or small molecular weight organic compounds. The compounds and molecules may be further characterized by their ability to increase or decrease legumain activity in order to determine whether they act as an agonist or an antagonist.

Legumain may be purified or be present in mixtures, such as in cultured cells, tissue samples, body fluids or culture medium. Assays may be developed that are qualitative or quantitative, with the latter being useful for determining the conversion rate or the binding parameters (affinity constants and kinetics) of the agent in its interaction with legumain and for quantifying levels of legumain in mixtures. Assays may also be used to detect fragments, analogs and derivatives of legumain and to identify new legumain family members.

Legumain nucleic acids are also useful for identification of factors that interact with the legumain promoter and that modulate legumain expression. Such factors may be intracellular proteins such as DNA binding proteins that interact with regulatory sequences that control legumain transcription, for example, the legumain promoter. As an example, hybrid constructs may be used that include a nucleic acid encoding the legumain promoter fused to a nucleic acid encoding a marker protein. The legumain promoter can be found within the genomic nucleotide sequence for human legumain that is available in the NCBI database at accession number NT 026437 (gi: 29736559). See website at ncbi.nlm.nih.gov. The marker protein can be any marker protein available to one of skill in the art. For example, the marker protein can be luciferase, green fluorescence protein (GFP) or CAT.

Such hybrid constructs are used for in vitro or in vivo transcription assays to identify factors that modulate legumain expression. Factors that depress or diminish legumain expression are particularly useful. Expression or transcription levels can be assessed using any method available to one of skill in the art for measuring RNA levels. For example, RNA levels can be assessed by northern analysis, reverse transcriptase analysis, reverse transcriptase coupled with polymerase chain reaction (RT-PCR) analysis and other methods. Chemical libraries can be screened using such methods for small molecule compounds that block legumain transcription.

Compositions

The prodrugs and compounds of the invention as well as inhibitors of legumain can be formulated as pharmaceutical compositions and administered to a mammalian host, such as a human patient in a variety of forms adapted to the chosen route of administration. Routes for administration include, for example, oral, parenteral, intraperitoneal, intravenous and intraarterial routes.

Solutions of the agents or their salts can be prepared in water or saline, and optionally mixed with a nontoxic surfactant. Formulations for intravenous or intraarterial administration may include sterile aqueous solutions that may also contain buffers, liposomes, diluents and other suitable additives.

The pharmaceutical dosage forms suitable for injection or infusion can include sterile aqueous solutions or dispersions comprising the active ingredient that are adapted for administration by encapsulation in liposomes. The ultimate dosage form should be sterile, fluid and stable under the conditions of manufacture and storage.

Sterile injectable solutions are prepared by incorporating the agents and inhibitors in the required amount in the appropriate solvent with various of the other ingredients, as required, followed by filter sterilization.

Useful dosages of the agents and inhibitors can be determined by comparing their in vitro activity, and in vivo activity in animal models. Methods for the extrapolation of effective dosages in mice, and other animals, to humans are known to the art; for example, see U.S. Pat. No. 4,938,949. The compound can be conveniently administered in unit dosage form.

The desired dose may conveniently be presented in a single dose or as divided doses administered at appropriate intervals, for example, as two, three, four or more sub-doses per day. The sub-dose itself may be further divided, for example, into a number of discrete loosely spaced administrations; such as multiple oral, intraperitoneal or intravenous doses. For example, it is desirable to administer the present compositions intravenously over an extended period, either by continuous infusion or in separate doses.

In some instances, the agents and inhibitors can be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, they may be combined with one or more excipients and used in the form of ingestible tablets, buccal tablets, troches, capsules, elixirs, suspensions, syrups, wafers, and the like. Such compositions and preparations may contain at least 0.1% of active compound. The percentage of the compositions and preparations may, of course, be varied. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

The therapeutically effective amount of prodrug, compound, or inhibitor necessarily varies with the subject and the disease or physiological problem to be treated. As one skilled in the art would recognize, the amount can be varied depending on the method of administration. The amount of the agent or inhibitor for use in treatment will vary not only with the route of administration, but also the nature of the condition being treated and the age and condition of the patient and will be ultimately at the discretion of the attendant physician or clinician.

The pharmaceutical compositions of the invention can include an effective amount of at least one of the agents of the invention, or two or more different agents of the invention. These compositions also include a pharmaceutically effective carrier.

The invention will be described with reference to the following non-limiting examples.

EXAMPLE 1

Legumain is Expressed in Tumors

Example 1 demonstrates that legumain is over-expressed in human tumors.

Materials and Methods
Reagents and Cell Lines

Rabbit polyclonal antisera against human legumain, as well as 293 cells stably expressing human legumain, were kindly provided by Dr. D. Roodman (Department of Medicine and Hematology, University of Texas Health Science Center, San Antonio, Tex.). A legumain substrate peptide was synthesized by and purchased from Bachem (King of Prussia, Pa.). Doxorubicin was purchased form Sigma. Costar migration chambers were obtained from Corning Incorporated (Corning, N.Y.). Vitrogen was obtained from Cohesion Technologies (Palo Alto, Calif.). Mouse monoclonal antibody specific for human integrin $\beta1$ was obtained from Dr. R. Klemke (The Scripps Research Institute). The DMEM media was obtained from Invitrogen (Carlsbad, Calif.). The CT26 murine colon carcinoma cell line was kindly provided by Dr. R. Reisfeld (The Scripps Research Institute). The 293 cells used to construct tetracycline-regulated cell lines expressing legumain were obtained from Stratagene (La Jolla, Calif.). Multiple tumor tissue arrays were provided by Cooperative Human Tissue Network, National Cancer Institute.

Rapid Isolation of Tumor Endothelial Cells and mRNA Extraction

CD31 antibody coated Dynabeads were prepared by mixing 300 µl bead suspension with 500 µl PBSA (PBS, 1% BSA). Biotinylated anti mouse CD31 antibody (20 µg) was added to the suspension and association of antibody to beads was for 20 minutes at 4° C. The beads were washed 3 times with PBS to remove unbound antibody. CT26 tumors grown to ~1.5 cm greatest diameter were surgically removed and cooled to 4° C. for following steps, and the tumor minced into 1 mm$^3$ bits with sterile scissors. The minced tumor was gently pressed through metal meshes and filtered through a 40 µm Falcon cell strainer (Becton Dickinson, Franklin Lakes, N.J.) to rapidly recover the single cell suspensions. Streptavidin conjugated paramagnetic Dynabeads (Dynal, Lake Success, N.Y.) coated with biotinylated anti-mouse CD31 antibody (Mec 13.3, PharMingen, La Jolla, Calif.) were immediately added to the single cell suspensions. Capture by beads of CD31 positive cells was conducted at 4° C. for 20 minutes with gentle agitation. Beads with bound CD31 positive cells were recovered with a magnetic trap column and washed three times with cold phosphate buffered saline (PBS). Unbound CD31 negative cells were collected separately and were recovered by centrifugation at 1000 rpm for 3 minutes. Both CD31 positive and CD31 negative cells were used for mRNA extraction (Qiagene mRNA direct kit). The concentration of mRNA was quantified with RiboGreen RNA quantification reagents (Molecular Probes, Eugene, Oreg.).

Differential Gene Expression Profiling Using Restriction Fragment Differential Display Five hundred ng mRNA was used for differential profiling using the displayPROFILE method (Display Systems Biotech, Vista, Calif.). The mRNA was first used to synthesize double stranded cDNA. The resultant double stranded DNA was digested with Taq I and adaptors were ligated onto the fragment ends. Display primer was used to PCR amplify the gene fragment profiles, which were then displayed on a 6% sequencing gel. Differentially displayed bands were cut from the sequencing gel and extracted with 50 μl water for 15 min in a boiling water bath. The fragments were reamplified with the same set of primers and then electrophoresed on 4% agarose gels. The amplified fragments were recovered from the gels and cloned into a pCRII vector by the Topo cloning method (Invitrogen, Carlsbad, Calif.). The vectors were then sequenced and BLAST searches performed with NCBI database to identify genes.

Histological and Immunohistochemical Analysis

Immunohistochemical staining was performed on both formalin fixed and unfixed frozen 5 μm thick sections on poly-L-lysine slides. For endothelial identification, biotinylated rat anti-mouse CD31 monoclonal antibody (MEC 13.3) was used with fluorescein conjugated streptavidin as the secondary reporting reagent. Rabbit anti-legumain antisera was prepared by immunization with purified human legumain produced in E. coli (Choi et al., 1999). This antisera recognized both mouse and rat legumain in frozen sections, as well as human legumain in formalin fixed sections. For staining of legumain in both frozen and formalin fixed sections, rabbit polyclonal anti-legumain antisera was used at 1:500 dilution followed by biotinylated anti-rabbit IgG as the second antibody. The reaction was visualized with Texas-red conjugated streptavidin and the slides were analyzed by laser scanning confocal microscope (Bio-Rad, Hercules, Calif.). For chromogenic staining, the rabbit polyclonal anti-legumain antibody was followed by a biotinylated goat anti rabbit antisera (Vector, Burlingame, Calif.). Streptavidin conjugated peroxidase was used and developed with the substrate BAD (Vector, Burlingame, Calif.).

Western Blot Analysis

Proteins were dissolved in 2×SDS sample buffer for SDS PAGE analysis using gradient (8-16%) Tris-glycine gels. Following electrophoresis, the proteins were transferred to nitrocellulose membranes, and blocked with non-fat milk. The anti-legumain antisera was used as the first antibody and was incubated with membrane for one hour (1:1,000 dilution). The blot was washed three time with PBS, incubated with streptavidin-peroxidase for 15 min and developed by the ECL method (Sigma, St. Louis, Mo.).

Statistical Analysis

Statistical significance of data in this and other Examples was determined by the two-tailed Student's t test.

Results

Over-Expression of Legumain in Solid Tumors

Figure 1B:
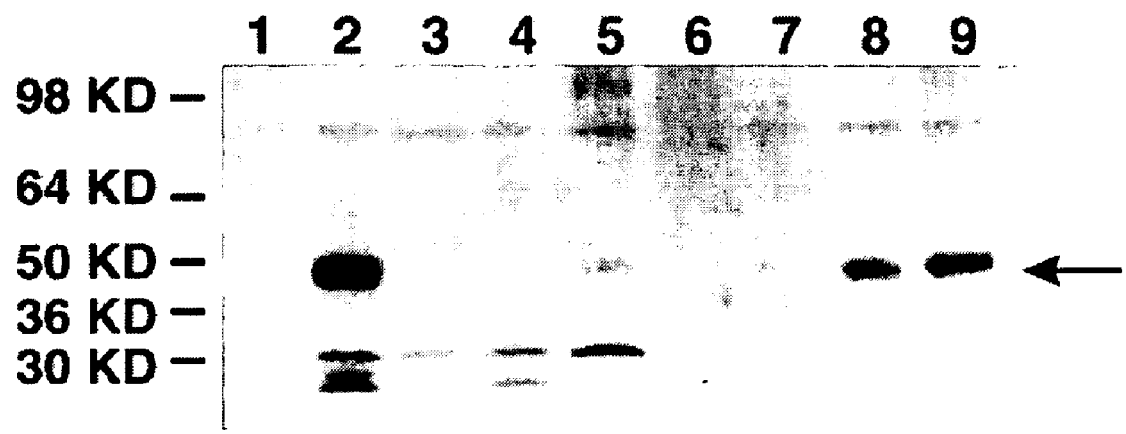
Figure 1C:
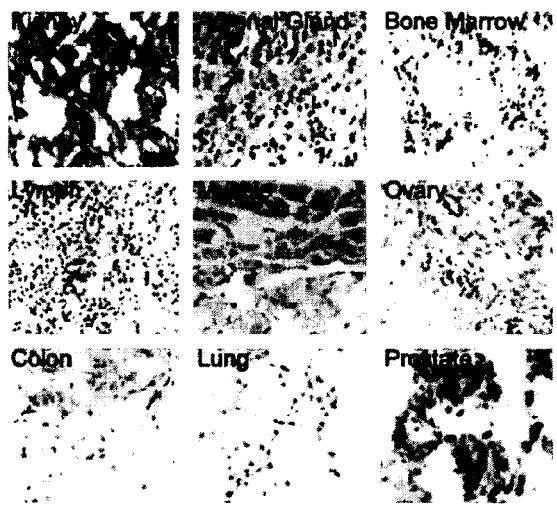
Figure 1D:
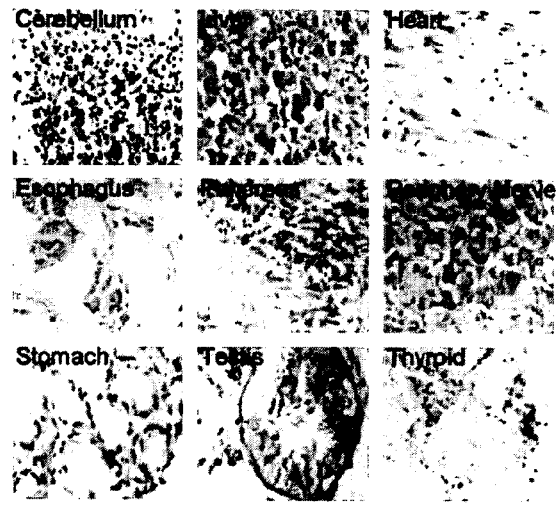
Figure 1E:
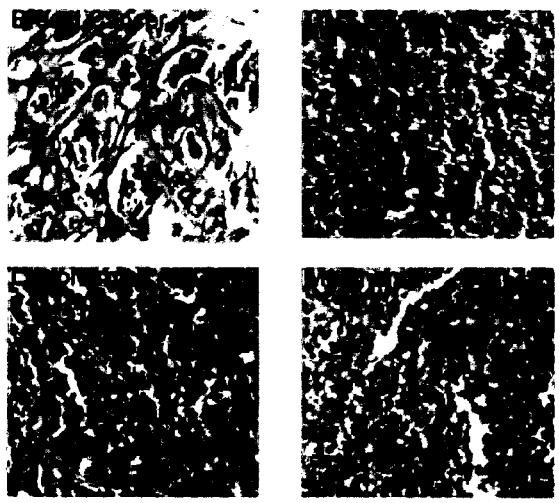
Figure 1F:
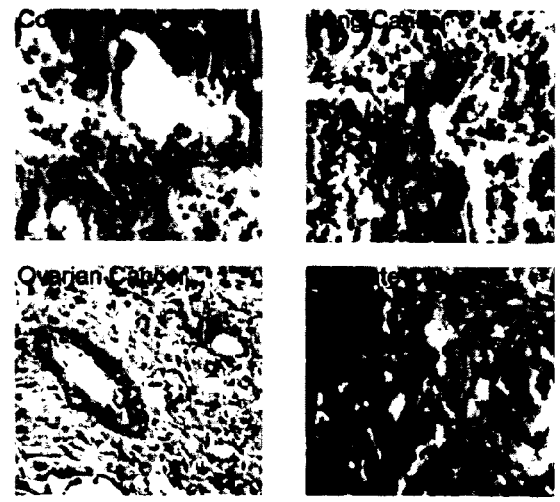

Use of restriction fragment differential display (Wrang et al., 2001; Gravesen et al., 2000; Zhang et al., 1998; Theissen et al., 1997) demonstrated that legumain is highly expressed in vivo in the CT26 murine colon carcinoma. Immunohistochemical studies of the CT26 tumor indicated that legumain is expressed by both tumor cells and, frequently, by tumor associated endothelial cells, both intracellularly and on the cell surface (FIG. 1A). Legumain over-expression in mouse tumors was confirmed by Western blot analysis. Legumain was also expressed by some normal mouse tissues (FIG. 1B). Legumain expression was not detected in the CT26 cell line in culture that was used to generate the syngeneic mouse colon carcinoma model, and legumain expression was not detected in other tumor cell lines in culture that were tested.

The surprising and unexpected up-regulation during tumor development in vivo suggests an in vivo environmental response. Legumain appears to be a stress responsive gene, because, although not detectable in cultured cells under typical tissue culture conditions, its expression was markedly elevated in cells subjected to environmental stress, such as serum starvation or in vivo growth.

To characterize legumain expression in normal human tissues and tumors, human tumor tissue arrays were analyzed immunohistochemically with anti-legumain antisera (FIG. 1C-F). While legumain expression was sparse in normal tissues, its expression was highest in the kidney. Legumain was also detected in liver and spleen, agreeing with published results (Chen et al., 1997; Chen et al., 1998).

Notably, legumain was highly expressed in the majority of human tumor tissue panels analyzed, which encompassed a wide variety of solid tumors (Table 3). Expression was highest for prostate carcinomas and positive for most breast and colon carcinoma specimens. All central nervous system malignancies were also positive for legumain expression.

TABLE 3

Legumain detection in human tumors.

| Carcinoma Type | Number analyzed | Number positive | Percentage positive | Degree of positivity |
|---|---|---|---|---|
| Breast carcinoma | 43 | 43 | 100% | +++ |
| Colon carcinoma | 34 | 32 | 95% | +++ |
| Lung carcinoma | 24 | 14 | 58% | +++ |
| Prostate carcinoma | 56 | 42 | 75% | ++++ |
| Ovarian carcinoma | 23 | 17 | 73% | ++ |
| CNS tumors | 8 | 8 | 100% | ++ |
| Lymphoma | 14 | 8 | 57% | + |
| Melanoma | 12 | 5 | 41% | + |

Cellular Distribution of Legumain

Figure 2A:
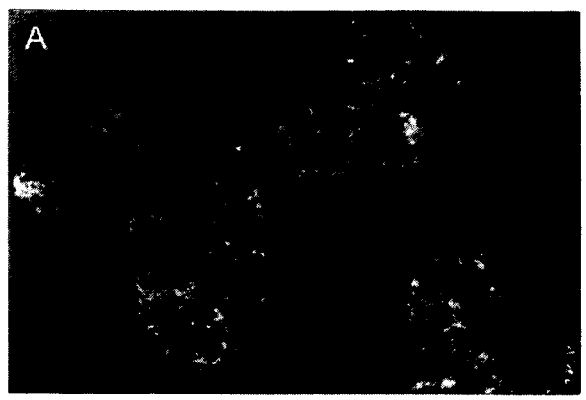
FIG. 2A-G illustrates the cellular distribution and activity of legumain.
Figure 2B:
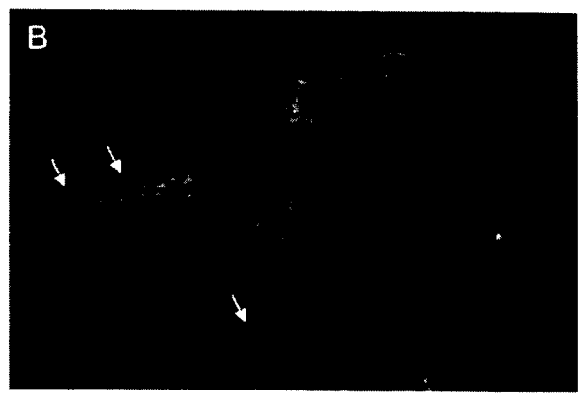
Figure 2C:
Figure 2D:
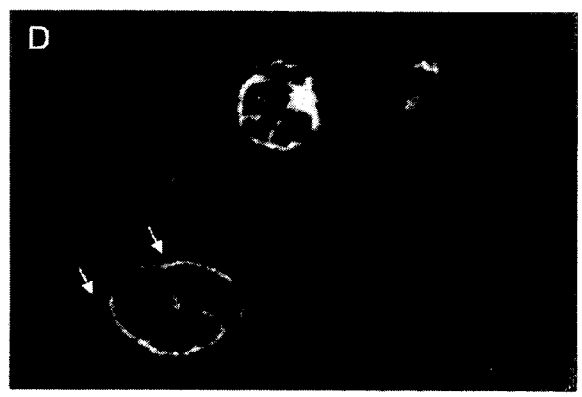

Legumain was most abundantly visualized associated within intracellular membranous vesicles (FIG. 2A), consistent with its proposed function as a lysosomal protease. The delivery of membranous vesicles containing proteases, adhesion molecules, and actin binding proteins toward the leading edge of migratory cells has been implicated in cell locomotion (Nabi et al., 1999; Bretscher et al., 1998). The legumain positive membranous vesicles were often concentrated at the invadopodia of tumor cells (FIG. 2B). Unexpectedly, legumain was also observed in apparent association with cell surfaces (FIG. 2C), as well as with the actin cortex (FIG. 2D).

Figure 2E:
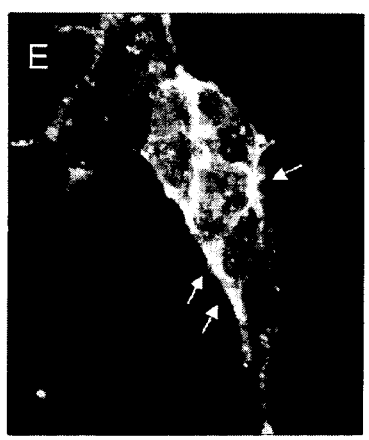

Double staining of legumain+ 293 cells with antibody against integrin β1 and anti-legumain antibody revealed the presence of legumain inside cells in a granular organelle resembling aggregated lysosomes, and also on the cell surface colocalized with β1 integrins (FIG. 2E). The potential binding of legumain to β1 integrins is provocative considering the RGD sequence motif present in legumain, a motif that might facilitate legumain association with cell surface integrins.

Therefore, it is herein disclosed for the first time that legumain is highly expressed by most human tumors. A high percentage of breast carcinomas, colon carcinomas, and central nerve system neoplasms strongly expressed legumain, with the highest expression found in prostate tumors. In contrast, legumain was weakly expressed or not observed in the normal tissues of tumor derivation. Furthermore, legumain expression was negative for the cell lines in culture that were used to generate the in vivo tumors, even though legumain was readily detected after those cell lines had been placed in vivo. These results are indicative of induction of gene expression by the in vivo tumor environment.

EXAMPLE 2

Legumain and Cell Migration, Tumor Invasion, and Metastasis

Example 2 discloses that legumain promotes cell migration and over-expression and is associated with enhanced tissue invasion and metastasis.

Materials and Methods

Cell Invasion and Mobility Assays

Cell migration and invasion assays were performed as described with modifications (Albini et al., 1987). Stock solutions (15 mg/ml) of Matrigel basement membrane matrix (Becton Dickinson, Bedford, Mass.) were stored at −80° C. in 100 µl aliquots. After thawing on ice, the stock was diluted 1:50 with cold serum-free culture media and immediately applied to each membrane insert (8 µm pore) that formed the upper chambers of the multi-well invasion assay plate. The Matrigel was incubated overnight in a sterile laminar tissue culture hood. The membranes were hydrated for 2 hours with 250 µl of serum-free medium and excess medium was removed by aspiration. Medium containing 10% FBS was added to the bottom of each well. A suspension of $10^5$ cells in 150 µl of serum-free medium was added to the upper chamber and incubated for 12 hours at 37° C., 5% $CO_2$. At the indicated times, the membrane inserts were removed from the plate and the non-invading cells were removed from the upper surface. Membrane associated cells were stained with 0.09% crystal violet for 30 minutes and washed twice with PBS. The invading cells were counted microscopically. Cell mobility assays were performed in a similar manner except the membrane inserts were not coated with Matrigel, and duration was shortened. In some assays, protease inhibitors were added to the invasion chamber at the beginning of the incubation.

Zymogram

Control 293 cells and legumain+ 293 cells were plated into 96 wells plates at 4,000 cells/well. The cells were allowed to attach overnight, then were serum starved for four hours. Zymogen forms of metalloproteinase 2 or 9 (Chemicon, Temecula, Calif.) were added at concentration of 0.1 µg/well with 50 µl reaction buffer (39.5 mM citric acid, 121 mM $Na_2HPO_4$, pH 5.8, 1 mM EDTA, and 0.8% $Na_2Cl$) and the reactions were continued for 10 minutes. The reactants were collected and mixed with an equal volume of SDS sample buffer and held at room temperature for 10 minutes then applied to a zymogram gel (10% Tris-Glycine gel with 0.1% gelatin substrate). After electrophoresis, the gel was washed briefly and incubated with 2.5% (v/v) Triton X-100 at room temperature for 30 minutes with gentle agitation. Digestion of the incorporated gelatin by activated collagenase was conducted in buffer (50 nM Tris, pH 7.25, 200 mM NaCl, 10 nM $CaCl_2$, 0.05% Brij-35, 0.02% $NaN_3$) overnight. The gel was stained with Coomassie Blue R250 (Novex, San Diego, Calif.) and the presence of a protease was readily observed as a clear band.

Results

Legumain Expression Promotes Cell Migration and Invasion

Figure 3A:
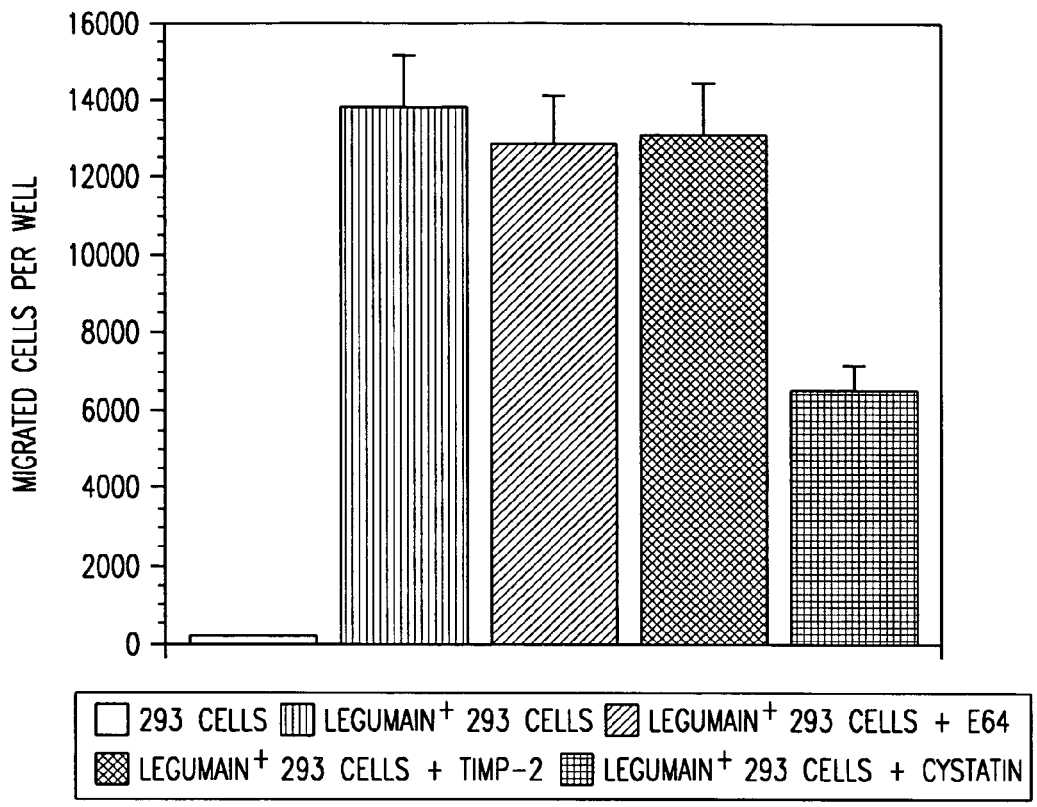
FIG. 3A-B shows that legumain expression promotes cell migration and invasion.

The effect of legumain expression on cell migration and invasion was investigated. In an in vitro migration assay, legumain+ 293 cells exhibited increased migration in comparison with wild type 293 cells. The enhanced migration was inhibited by cystatin, a known inhibitor of legumain protease function, weakly by TIMP-2 protein, but not by E64 (FIG. 3A).

Figure 3B:
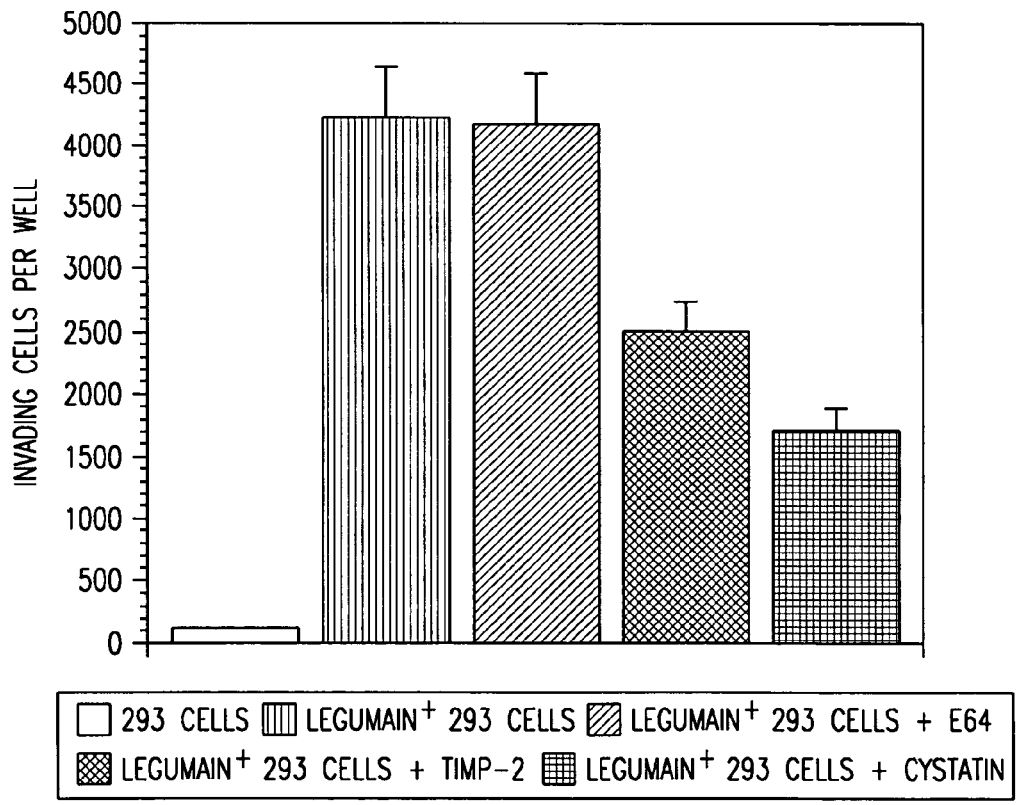

Next, control 293 cells and legumain+ 293 cells were evaluated in a modified Boyden chamber invasion assay. Legumain+ cells exhibited increased invasion of extracellular matrix. Such increased invasion was inhibited by cystatin (FIG. 3B), but to only a limited extent by TIMP-2. Again E64 was without effect. These experiments were repeated with a 293 cell line in which the transcription of legumain was conditionally regulated by tetracycline. Comparable results were obtained (data not shown).

Legumain Expression Correlates with Tumor Invasion and Metastasis

To explore the effects of legumain expression in vivo, legumain+ 293 cells and control 293 cells were injected subcutaneously into the backs of WEHI nude mice. Tumors appeared after 2-3 weeks. The initial rates of primary tumor growth were comparable. There was prominent legumain expression in the legumain+ 293 tumors. Weak but positive legumain expression was detectable in control 293 tumors, despite an absence of legumain expression by these cells in culture. These results were similar to the observations for the CT26 colon carcinoma cells. Histological analysis of more advanced tumors suggested a lower rate of apoptosis for legumain+ 293 tumors compared to control 293 tumors.

Figure 4A:
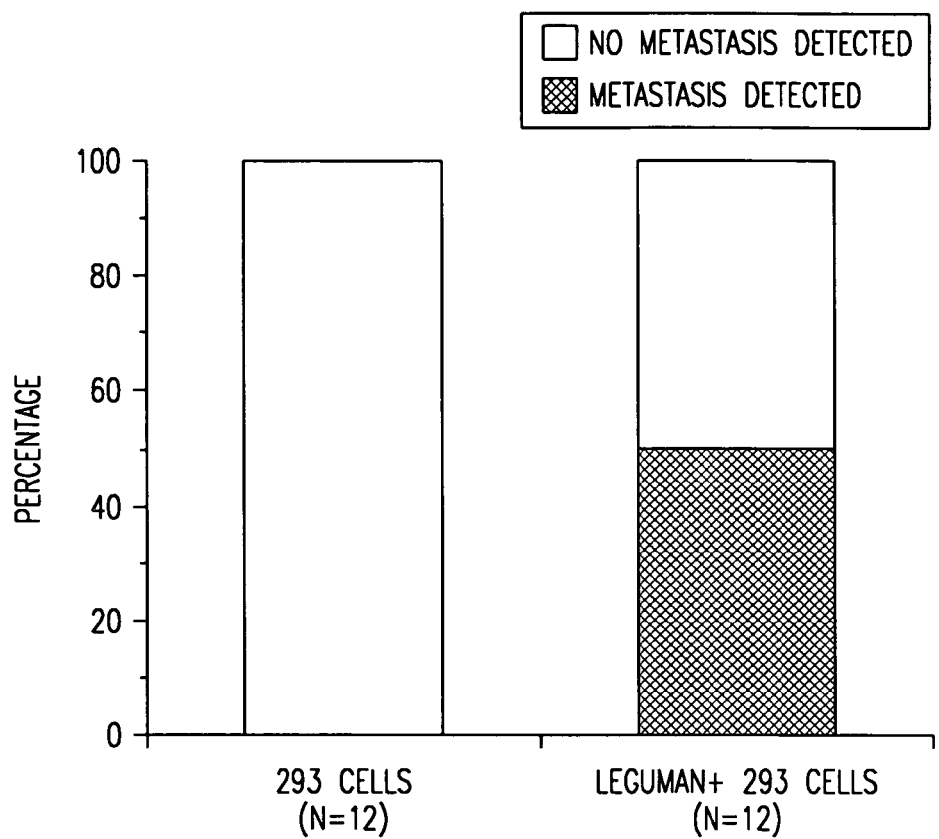
FIG. 4A-C shows that legumain enhances tumor invasion and metastasis in vivo.
Figure 4B:
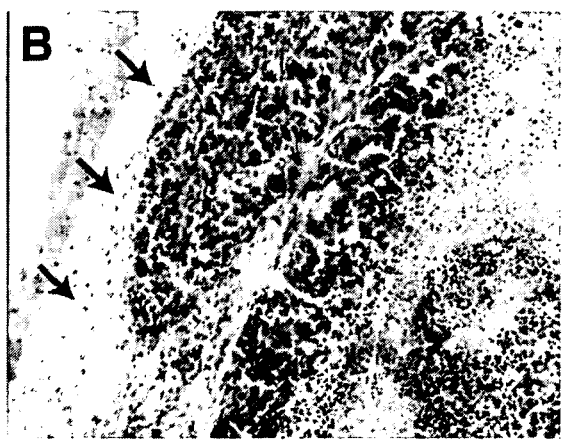
Figure 4C:

Legumain+ 293 tumors frequently metastasized in vivo in contrast to control 293 tumors. At necropsy, 50% of legumain+ 293 tumor bearing mice had metastatic nodules in distant organs (FIG. 4A), predominantly in the lung and liver. In contrast, no metastatic nodules were observed in distant organs within animals that received control 293 cells. The increased invasion and metastasis associated with legumain over-expression is consistent with legumain-facilitated tumor metastasis and progression. The more invasive legumain+ 293 tumors frequently invaded muscles and frequently lacked the well defined pseudo-encapsulation observed with control 293 tumors (FIGS. 4B and 4C). This more invasive tumor behavior was evident in early as well as later stage tumors.

Activation of Progelatinase A by Legumain

Figure 2F:
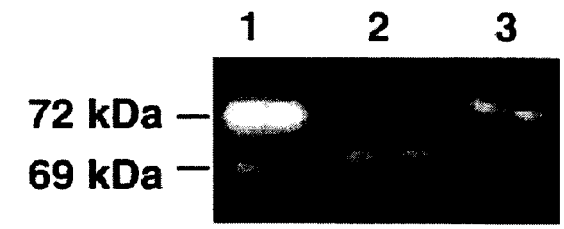
Figure 2G:
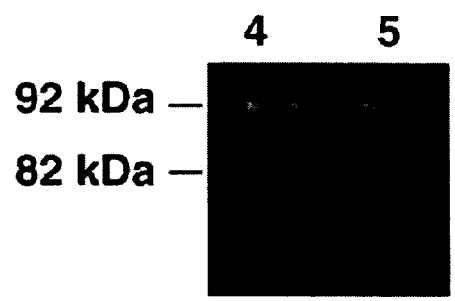

Tumor cell surface-associated proteases may degrade extracellular matrix proteins, for example, gelatinase A and cathepsins. Legumain does not degrade gelatin directly when analyzed in a gelatin zymogram (data not shown). The activation of progelatinase A requires cleavage of an asparaginyl bond (Nagase et al., 1997). Whether cell surface bound legumain can convert the 72 kDa zymogen to the 62 kDa active enzyme was examined. Cells expressing legumain, as well as control cells, were deposited in 96 well plates. After attachment and serum starvation, the culture media was removed. Zymogen forms of gelatinase A and B were incubated with the cells for 10 minutes, and the reaction products were analyzed by zymography. Generation of the 62 kDa active enzyme was observed for cells expressing legumain, and the activation was inhibited by cystatin (FIG. 2F). No effect of legumain on zymogen gelatinase B was detected (FIG. 2G).

Discussion

Proteases have been implicated in many aspects of tumor cell biology (Chang et al., 2001). Thus, a protease that is highly expressed by tumor cells or tumor vascular endothelial cells might contribute to tumor cell progression through processing of signaling molecules and their receptors, thereby influencing cellular responses. Such effects might also result in diminished apoptosis (Hanahan et al., 2000), thereby enhancing tumor growth.

Evidence is presented herein for not only atypical expression, but also for the participation of legumain in effector functions and as an apparent regulator of cellular behavior in migration and tissue invasion. Cells that highly express legumain exhibited enhanced migratory and invasive properties. A correlation between tumor invasion and metastasis with the presence of cysteine endopeptidases (particularly cathepsins B and L) has been observed (Mai et al., 2000). Hydrolysis of asparaginyl bonds is prominent in the post-translational processing of cathepsin B, D, and H (Chen et al., 1997; Chen et al., 1998; Yonezawa et al., 1988). Legumain might activate local cysteine protease zymogens to their active two chain protease forms.

In addition to the established plasminogen/plasmin system and the metalloproteinase system, a cysteine protease cascade may represent an additional tumor invasion/metastasis cascade. As described, a 62 kDa activated gelatinase A enzyme was observed in cells expressing legumain, and such activation was inhibited by cystatin (FIG. 2F). No effect of legumain on zymogen gelatinase B was detected (FIG. 2G). Hence, legumain activates the gelatinase A zymogen, an important mediator of extracellular matrix degradation. The activation mechanism of gelatinase A by legumain differs from that involved with the membrane type matrix metalloproteinases (Itoh et al., 1998). This may be important for tumor cell adaptation to a more invasive and metastatic phenotype.

Legumain-promoted cell migration and invasion can be partially inhibited by cystatin and TIMP-2. The inhibition of mammalian legumain by cystatin is due to a novel second reactive site (Alvarez-Fernandez et al., 1999). Another cysteine inhibitor, E64, has no affect on legumain or cell migration. Hence, the increased cell migration in legumain+ cells is not due to a member of the papain family of cysteine proteases that are characteristically susceptible to E64 inhibition.

Analysis by site-directed mutagenesis of the catalytic residues of mammalian legumain suggests a catalytic dyad exists with the motif His-Gly-spacer-Ala-Cys (SEQ ID NO:1). The presence of this motif is also found in the catalytic sites of the caspases, the aspartate-specific endopeptidases central to the process of apoptosis in animal cells, as well as in the families of clostripain and gingipain which are arginyl/lysyl endopeptidases of pathogenic bacteria. However, legumain is notably distinct from other lysosomal cysteine proteases. In particular, its catalytic activity is unique in that it is the only asparaginyl endopeptidase identified to date. Moreover, the sequence for legumain is conserved through evolution. Its conservation and unique enzymatic activity indicate legumain may have a significant biologic function.

Animal tumor models generated with cells over-expressing legumain had more vigorous and invasive growth and metastasis in vivo behavior than similar tumor cells that did not overexpress legumain. These results indicate that the proteolytic function of legumain may activate other protease zymogens. The inhibitory effect of cystatins on tumor cells (Sexton et al., 1997; Coulibaly et al., 1999) is consistent with the involvement of legumain and perhaps other cysteine proteases in tumor invasion and metastasis.

Tumor invasion and metastasis are critical determinants of cancer lethality, linked to 90% of human cancer deaths (Sporn et al., 1996). Invasion and metastasis are considered as associated properties of tumor cells as they utilize similar processes involving physical attachment of cells to their environment through cell adhesion molecules (CAMs) and activation of extracellular proteases (Hanahan et al., 2000). Increased expression of proteases and down regulation of protease inhibitors is commonly observed in tumors (Yano et al., 2001; Chamber et al., 1997). Notably, cell surface proteases are often associated with invasive and metastatic tumor cells (Chang et al., 2001). Some proteases are linked to other properties of tumors such as angiogenesis (Stetler-Stevenson et al., 1999) and growth signaling (Werb et al., 1997) as perhaps with legumain.

Protease zymogens are dependent on limited proteolytic activation for conversion to the functional state. Protease cascades are characteristic of many biologic pathways, such as the coagulation, apoptosis, and complement cascades. Similar cascades appear to be involved in tumor invasion and metastasis. Characterization of the later is complicated by the diversity of neoplasms. However, comprehensive profiling of protease expression and function may advance understanding of tumor invasion and metastasis.

Some metalloproteinase inhibitors have demonstrated tumor stasis in animal models. Similarly, legumain represents a target for inhibition of growth and metastasis based on its up-regulation associated with tumor growth and unique restricted specificity. Legumain functions both extracellularly and intracellularly. Therefore, a cell-permeable inhibitor might extend the efficacy observed with cystatin, as the latter is cell impermeable and has shown limited inhibition of in vitro cell migration and invasion.

Tumor cells with higher legumain levels appear more resistant to apoptosis. Although the precise molecular pathway has yet to be defined for this effect, lysosomal proteases are known to participate as effector enzymes in apoptosis (Foghsgaard et al., 2001; Castino et al., 2002). In another context, others have been observed to inhibit apoptosis (Zhu et al., 2000). Thus, the sub-cellular localization of legumain may determine its targets and thereby its effects on the apoptosis cascades.

EXAMPLE 3

Tumoricidal Effects of a Prodrug

Legumain's unique functional properties and high level expression in a wide range of human tumors makes it a potential candidate target for enzymatic activation of a prodrug that can provide tumor eradicative therapy.

The integrity of the amino group of doxorubicin is essential for function. It has been shown that doxorubicin tolerates the addition of a leucine residue at this site. However incorporation of additional amino acids abolishes cytotoxic activity (de Jong et al., 1992; Denmeade et al., 1998).

In this Example, a prototype prodrug was synthesized by addition of an asparaginyl endopeptidase substrate peptide to doxorubicin. Upon exposure to legumain, the agent was converted to an active cytotoxic leucine-doxorubicin molecule. The prodrug had markedly reduced toxicity compared to doxorubicin, but it was effectively tumoricidal in a murine colon carcinoma model where it was presumably cleaved to form the leucine-doxorubicin cytotoxin. Therefore, according to the invention, legumain is a new target for tumoricidal prodrug development and therapy.

Materials and Methods

Prodrug Synthesis

N-(-t-Butoxycarbonyl-L-alanyl-L-alanyl-L-asparaginyl-L-leucyl)doxorubicin (SEQ ID NO:7) was synthesized as follows. To cold (0° C.) solution of t-Butoxycarbonyl-L-alanyl-L-alanyl-L-asparaginyl-L-leucine (43 mg, 95 µmol) and 4-Methylmorpholine (20 µL, 200 µmol) in 5 mL DMF was added O-Benzotriazol-1-N,N,N',N'-tetramethyluronium hexafluorophosphate (HBTU) (54 mg, 142.5 µmol). After 10 min, doxorubicin hydrochloride (50 mg, 86 μmol) was added and the mixture was stirred for 2 h at room temperature in the dark. The solution was diluted with 30 mL of EtOAc and washed with water. The solvent was evaporated, and solids were dried over $MgSO_4$ and purified over silica gel using $CHCl3/MeOH$ (90/10) while protected from light to yield 65 mg of compound 1 (75% yield). $^1H$ NMR (600 MHz, $CD_3OD$, δ): 0.82 (d, 3H, J=6.1), 0.88 (d, 3H, J=6.6), 1.28-1.35 (m, 9H), 1.43 (s, 9H), 1.59-1.74 (m, 4H), 2.05 (m, 1H), 2.17 (m, 1H), 2.36 (d, 1H, J=14.5), 2.67 (m, 1H), 2.79 (m, 1H), 2.91 (d, 1H, J=18.0), 3.04 (d, 1H, J=18.0), 3.62 (m, 1H), 4.01-4.04 (m, 4H), 4.11 (m, 1H), 4.22-4.32 (m, 3H), 4.59 (dd, 1H, J=5.9, 7.2), 4.74 (d, 2H, J=4.4), 5.08 (s, 1H), 5.39 (d, 1H, J=3.1), 7.51 (d, 1H, J=8.8), 7.78 (dd, 1H, J=7.9, 7.9), 7.86 (d, 1H, J=7.5). Preparation HRMS (MALDI) calculated for $C_{48}H_{64}N_6O_{18}$ $[M+Na]^+$ is 1035.4169, and found is 1035.4234. The compounds were purified by semi-preparative HPLC.

Cytotoxic Assays

The WST-1 cell proliferation reagent (Roche Molecular Chemicals, Germany) was used to determine cell proliferation by quantification of cellular metabolic activity. Control 293 cells and legumain+ 293 cells were cultivated in microtiter plates ($5 \times 10^3$ cells per well in 100 μl) and were incubated with serial concentrations of legubicin or doxorubicin for 48 h. Subsequently, 10 μl of WST-1 solution (1 mg/ml WST-1, 25 μM-methyldibenzopyrazine methyl sulfate) was added per well, and mixtures were incubated for an additional 4 h. The tetrazolium salt WST-1 (4-[3-(4-Iodophenyl)-2-(4-nitrophenyl)-2H-5-tetrazolio-1,3-benzene disfonate) was cleaved by the mitochondrial succinate-tetrazolium-reductase system to formazan in cells which directly correlates to the number of metabolically viable cells in the culture. The amount of formazan salt was quantified in three replicates by absorbance at 450 nm using a micro-plate reader (Molecular Devices, Palo Alto, Calif.). All results were derived from replicate experiments with similar results.

Animal Models

The CT26 syngeneic murine colon carcinoma model was generated and maintained in The Scripps Research Institute animal facility. Balb/C mice aged 4 to 6 weeks from the breeding colony were inoculated with 500,000 syngeneic CT26 tumor cells per site subcutaneously in the back. Treatment was initiated when the tumors reached 4 mm in diameter through bolus intraperitoneal injection of the indicated reagents. Treatment was repeated at 2 day intervals. The human 293 tumor models were generated in WEHI nude mice (The Scripps Research Institute breeding colony). Either legumain+ 293 cells or control 293 cells ($10^6$ cells/site) were inoculated subcutaneously on the back. Tumor growth and physical signs were monitored daily including any gross evidence of tumor necrosis, local tumor ulceration as well as evidence of toxicity including mobility, response to stimulus, eating, and weight of each animal. These procedures have been reviewed and approved by the Institutional Animal Care and Use Committee at The Scripps Research Institute. The work was conducted in The Scripps Research Institute facilities which are accredited by the Association for the Assessment and Accreditation of Laboratory Animal Care. The Scripps Research Institute maintains an assurance with the Public Health Service, is registered with the United States Department of Agriculture and is in compliance with all regulations relating to animal care and welfare.

Results

Model Prodrug Activation by Legumain

Figure 5A:
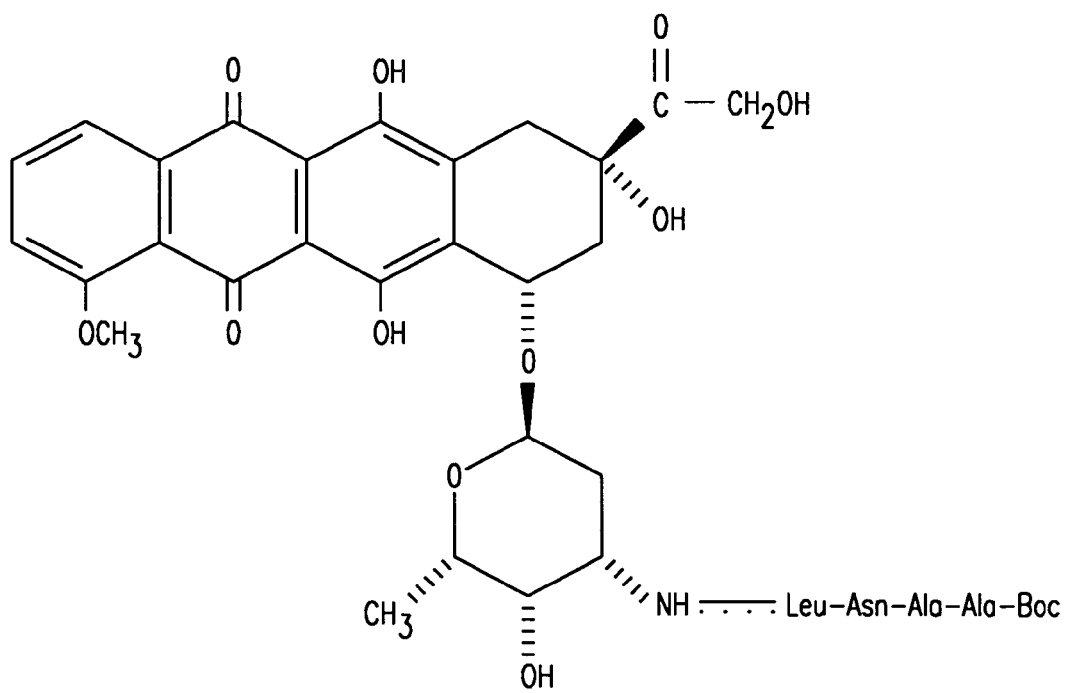
FIG. 5A provides a chemical structure for the legubicin prodrug that can be activated by the asparaginyl endopeptidase legubicin, where an amino group of the doxorubicin is covalently bonded to the carboxy terminus of a leucine residue.

The functional capacity of tumor cell-associated legumain was explored based on the novel asparaginyl specific endopeptidase activity of legumain. The amino group of doxorubicin is critical for function. However a leucine residue can be added with retention of cytotoxicity. The prodrug, N-(-t-Butoxycarbonyl-L-alanyl-L-alanyl-L-asparaginyl-L-leucyl) doxorubicin (SEQ ID NO:7), was synthesized by addition of an asparaginyl endopeptidase substrate peptide Boc-Ala-Ala-Asn-Leu to the amino group of doxorubicin through a peptide bond at carboxy terminus of leucine. Upon cleavage by legumain, the prodrug is converted to a leucine-doxorubicin molecule, thereby regaining cytotoxic function. In addition, the presence of the Boc at the amino terminus prevents aminopeptidase hydrolysis of the peptidyl component. This prodrug is designated Legubicin (FIG. 5A).

Figure 5B:
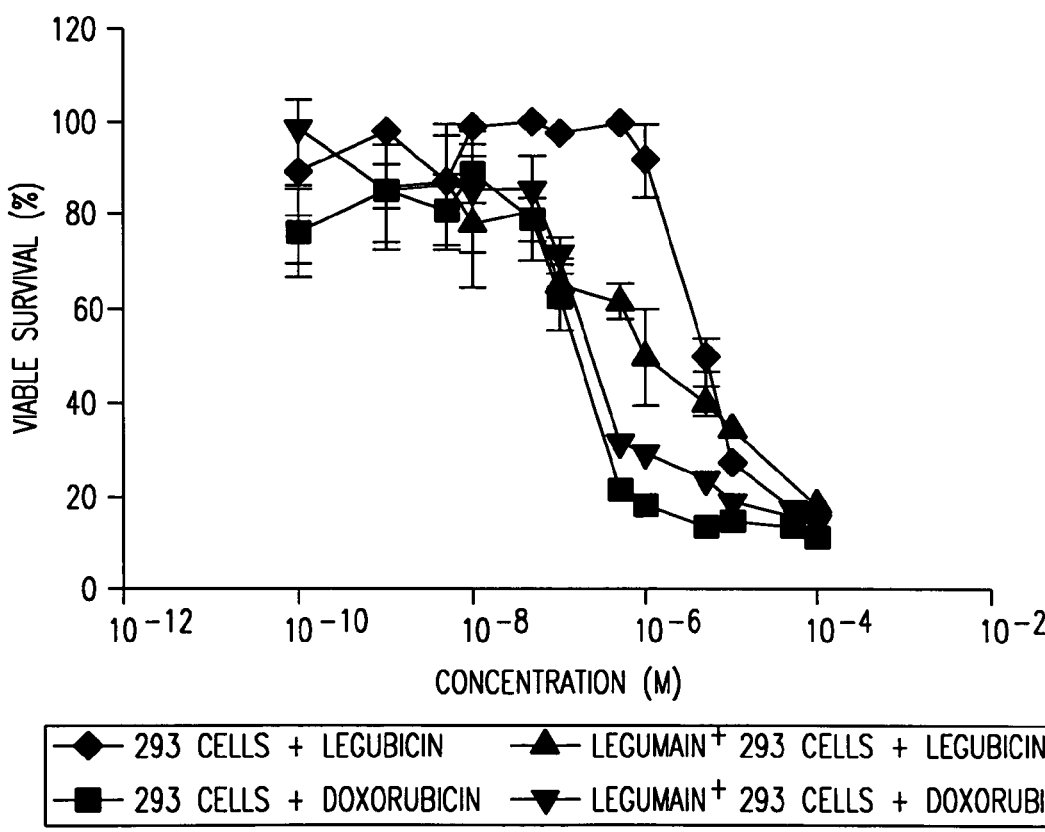
FIG. 5B graphically illustrates the cytotoxicity of legubicin and doxorubicin in legumain$^+$ 293 cells and in control 293 cells. The following symbols were employed in the graph: ♦ 293 cells treated with legubicin; ■ 293 cells treated with doxorubicin; ▲ legumain expressing 293 cells treated with legubicin; and ▼ legumain expressing 293 cells treated with doxorubicin. Cytotoxic activity of legubicin is much higher on legumain$^+$ cells than on control 293 cells, consistent with legumain activation of the prodrug by these cells.

First, the cytotoxic activity of doxorubicin and legubicin upon activation by legumain was analyzed in vitro using legumain+ 293 cells and control 293 cells (FIG. 5B). The effect of doxorubicin on both 293 cell types was similar, with legumain+ cells only slightly more resistant to doxorubicin. In contrast, the cytotoxic effect of legubicin on control 293 cells was less than 1% of that of doxorubicin, indicating peptide conjugation had abolished the cytotoxic effect of the doxorubicin. The dose responsive curve of legubicin on control 293 cells was parallel to that of doxorubicin on both 293 cells, suggesting that the residual cytotoxicity may result from slight (~1%) doxorubicin contamination. In contrast, a profound cytotoxic effect of legubicin was observed for legumain+ 293 cells. The dose response curve of legumain+ cells challenged with legubicin differed from that for these cells exposed to doxorubicin.

Tumoricidal Effect of Legubicin In Vivo

Figure 6B:
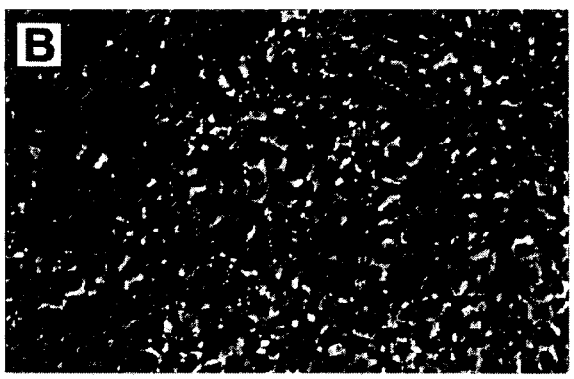

The in vivo effects of legubicin on normal and tumor bearing hosts and efficacy in tumor eradication was investigated using the CT26 murine syngeneic colon carcinoma model. Legubicin was very well tolerated in mice with much reduced toxicity compared to doxorubicin. Intraperitoneal injection of legubicin at 5 mg/kg three times at 2 day intervals induced complete growth arrest of the tumors with little evidence of toxicity (FIG. 6A1-6A3), as most readily evidenced by the absence of weight loss (FIG. 6A3). In contrast, doxorubicin failed to produce similar anti-tumor efficacy at doses approaching its maximum tolerable dose (MTD). When doxorubicin was administered by the same protocol and dosage as for legubicin, toxicity was fatal.

Figure 6C:
Figure 6D:
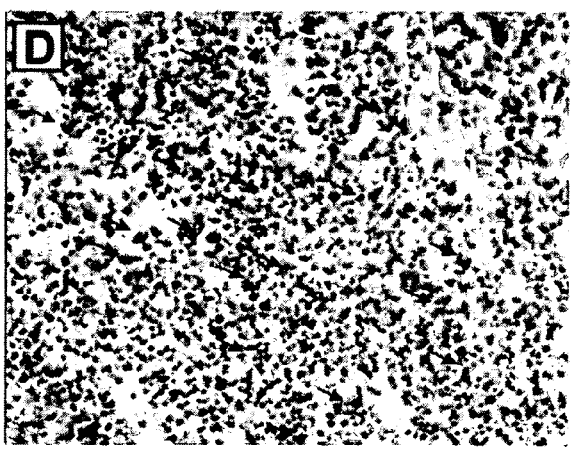
Figure 6E:
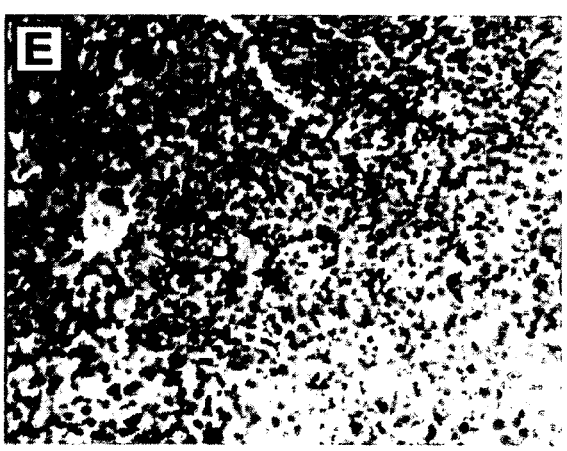

A single injection of 5 mg/kg legubicin induced more profound tumoricidal effects than animals given a comparable dose of doxorubicin (FIGS. 6B and 6C), as observed by histology. TUNEL assay analysis of tumor tissues revealed a higher apoptotic index for legubicin than for doxorubicin treatment (FIGS. 6D and 6E). Surprisingly, in organs that do express legumain, such as kidney and liver, no injury was evident (not shown). These observation indicate that legubicin has significantly improved safety and therapeutic indices compared to doxorubicin.

Discussion

The high level of legumain expression by tumor cells, coupled with its unusual and highly specific substrate requirement for catalytic function, makes it an attractive candidate for prodrug conversion in a therapeutic mode. Current cancer chemotherapeutic agents have significant undesirable cytotoxicity. A promising approach to increase selectivity is to exploit enzymes more highly expressed by tumor cells to achieve local prodrug activation to the active compound. Peptide conjugates of doxorubicin designed for activation by plasmin (de Groot et al., 1999; Chakravarty et al., 1983) and cathepsins (Satchi et al., 2001; Dubowchik et al., 1998a and 1998b) have been suggested. However, those conjugates are relatively deficient in target selectivity since plasmin generation is not tumor selective.

The doxorubicin prodrug exemplified herein was synthesized by incorporating a peptide extension to the amino group of doxorubicin. This agent, designated legubicin, was analyzed for cytotoxicity on cells not expressing legumain where it was less than 1% as toxic as doxorubicin. However, on cells expressing legumain, legubicin was profoundly cytotoxic, consistent with conversion to leucine-doxorubicin.

Intraperitoneal administration of legubicin at 5 mg/kg resulted in complete arrest of tumor growth without identifiable toxicity, such as weight loss, in contrast to doxorubicin treated mice. Legubicin administration produced profound tumor cell apoptosis as indicated by TUNEL assay. Unexpectedly, in organs containing cells that normally express legumain, such as kidney and liver, no injury was evident. Thus, legumain activation of this prodrug may require conditions not present in normal tissue. Prodrug activation may be carried out by secreted or cell surface associated legumain; whereas legumain appear to be localized in lysosomal vesicles in normal tissues. Legumain requires an acidic environment for optimal catalytic activity, which may not be present in normal tissues. Legubicin also appears to have an improved therapeutic index compare to its parent doxorubicin. Whereas clinical use of doxorubicin is limited by the its toxicity, a prodrug that preserves activity, but that has reduced toxicity is an attractive alternative.

EXAMPLE 4

Analysis of Substrate Specificity of Legumain Using Phase Displayed Substrate Libraries Legumain demonstrated an uniquely restricted specificity requiring an asparagine residue at the P1 position. However it does not hydrolyze all asparaginyl carboxyl peptide bonds of all protein substrates. Chen, J. M., et al., *Cloning, isolation, and characterization of mammalian legumain, an asparaginyl endopeptidase.* J Biol Chem, 1997. 272(12): p. 8090-8; 47; Mathieu, M. A., et al., *Substrate specificity of schistosome versus human legumain determined by P1-P3 peptide libraries.* Mol Biochem Parasitol, 2002. 121(1): p. 99-105. Many asparagine residues may not be accessible and able to form transition state analogues in most proteins. Amino acid preferences for parasite legumain indicate legumain has some degree of preference for the P2 and P3 positions, however can accept all residues except proline at the P1' position. Mathieu, et al. (2002); Schwarz, G., et al., *Characterization of legumain.* Biol Chem, 2002. 383(11): p. 1813-6.

The substrate specificity of mammalian legumain will be explored using combinatorial phage display peptide libraries that will be constructed by inserting a legumain recognition site between a Tissue Factor extracellular domain ($TF_{1-218}$) and fusion with a second gene III in M13 phage. $TF_{1-218}$ is particularly resistant to proteolysis. The legumain substrates library will contain two random amino acids flanking each side of a asparagine residue (XXNXX). Such a library has a modest library size of $1.6 \times 10^5$ different sequence combinations. DNA encoding these peptide sequences will be synthesized and cloned into the phage vector display $TF_{1-218}$ as a fusion protein with the second phage gene III coat protein.

The phage displayed substrate library will be immobilized in 96 well plates through anti-TF antibody, and recombinant legumain expressed by *Pichia* yeast will be used for proteolysis to release the susceptible phage from the plate. These phage will be plated and amplified. Individual phage will be selected and sequenced to detect the susceptible residues surrounding the asparagine residue. The motifs of highest frequency represent the more favorable sequences for legumain recognition. The identified peptide sequences will be confirmed with synthetic peptides and its binding kinetics will be characterized.

REFERENCES

Albini et al., Cancer Res, 47: 3239-3245, 1987.
Alvarez-Fernandez et al., J Biol Chem, 274: 19195-19203, 1999.
Asgian et al., J Med Chem, 45: 4958-4960, 2002.
Barrett et al., Biol Chem, 382: 727-733, 2001.
Beck et al., Eur J Immunol, 31: 3726-3736, 2001.
Bretscher et al., Curr Opin Cell Biol, 10: 537-541, 1998.
Cancer Facts & Figures, 2003: American Cancer Society.
Castino et al., Int J Cancer, 97: 775-779, 2002.
Chakravarty et al., J Med Chem, 26: 638-644, 1983.
Chambers et al., J Natl Cancer Inst, 89: 1260-1270, 1997.
Chang et al., Trends Cell Biol, 11: S37-43, 2001.
Chen et al., J Biol Chem, 272: 8090-8098, 1997.
Chen et al., Biochem J, 335: 111-117, 1998.
Chen et al., Biol Chem, 382: 777-783, 2001.
Choi et al., J Biol Chem, 274: 27747-27753, 1999.
Choi et al., J Bone Miner Res, 16: 1804-1811, 2001.
Coulibaly et al., Int J Cancer, 83: 526-531, 1999.
de Groot et al., J Med Chem, 42: 5277-5283, 1999.
de Jong et al., Cancer Chemother Pharmacol, 31: 156-160, 1992.
Denmeade et al., Cancer Res, 58: 2537-2540, 1998.
Dubowchik et al., Bioorg Med Chem Lett, 8: 3347-3352, 1998a.
Dubowchik et al., Bioorg Med Chem Lett, 8: 3341-3346, 1998b.
Foghsgaard et al., J Cell Biol, 153: 999-1010, 2001.
Gravesen et al., Microbiology, 146 (Pt 6): 1381-1389, 2000.
Hanahan et al., Cell, 100: 57-70, 2000.
Itoh et al., J Biol Chem, 273: 24360-24367, 1998.
Mai et al., J Biol Chem, 275: 12806-12812, 2000.
Manoury et al., Nature, 396: 695-699, 1998.
Nabi et al., J Cell Sci, 112: 1803-1811, 1999.
Nagase et al., Biol Chem, 378: 151-160, 1997.
Payne et al., Cancer Cell, 3: 207-212, 2003.
Satchi et al., Br J Cancer, 85: 1070-1076, 2001.
Sexton et al., Melanoma Res, 7: 97-101, 1997.
Sporn et al., Lancet, 347: 1377-1381, 1996.
Stetler-Stevenson et al., J Clin Invest, 103: 1237-1241, 1999.
Theissen et al., Methods Mol Biol, 85: 123-133, 1997.
Werb et al., Cell, 91: 439-442, 1997.
Wrang et al., J Neurosci Res, 65: 54-58, 2001.
Yano et al., Surg Today, 31: 385-389, 2001.
Yonezawa et al., J Biol Chem, 263: 16504-16511, 1988.
Zhang et al., Mol Biotechnol, 10: 155-165, 1998.
Zhu et al., Leuk Lymphoma, 39: 343-354, 2000.
U.S. Pat. No. 6,004,933
U.S. Patent Publication Number US 2003/0054387
PCT International Publication Number WO 00/64945
PCT International Publication Number WO 03/016335

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A prodrug compound, comprising cytosine arabinoside or doxorubicin linked to a legumain peptide substrate having a peptide consisting of amino acid sequence Ala-Ala-Asn-Leu (SEQ ID NO:5) and wherein legumain cleaves the peptide at the link between the Asn and another amino acid to generate active cytosine arabinoside or doxorubicin from the prodrug.

2. The compound of claim 1, wherein the prodrug is substantially non-toxic to non-legumain expressing animal cells.

3. The compound of claim 1, wherein the amino acid sequence comprises Boc-Ala-Ala-Asn-Leu (SEQ ID NO:4).

4. The compound of claim 1, wherein the amino acid sequence comprises succinyl-Ala-Ala-Asn-Leu (SEQ ID NO:8).

5. The compound of claim 1, wherein the peptide further comprises a protecting group.

6. The compound of claim 5, wherein the protecting group is an amino protecting group.

7. The compound of claim 5, wherein the protecting group is succinyl.

8. The compound of claim 5, wherein the protecting group is t-butoxycarbonyl.

9. The compound of claim 5, wherein the peptide further comprises an N-β-alanyl terminus.

10. A pharmaceutical composition, comprising the compound of claim 1 and a pharmaceutically acceptable carrier.

11. A method for treating a mammal having cancer comprising administering to the mammal the compound of claim 1 in amounts and at intervals effective to reduce or eliminate one or more of the symptoms associated with cancer.

12. The method of claim 11, wherein the cancer is a solid cancer.

13. The method of claim 11, wherein the cancer is breast cancer, colon cancer, lung cancer, prostate cancer, ovarian cancer, cancer of the central nervous system, lymphoma, or melanoma.

14. The method of claim 11, wherein the cancer is autoimmune deficiency syndrome-associated Kaposi's sarcoma, cancer of the adrenal cortex, cancer of the cervix, cancer of the endometrium, cancer of the esophagus, cancer of the head and neck, cancer of the liver, cancer of the pancreas, cancer of the prostate, cancer of the thymus, carcinoid tumors, chronic lymphocytic leukemia, Ewing's sarcoma, gestational trophoblastic tumors, hepatoblastoma, multiple myeloma, non-small cell lung cancer, retinoblastoma, or tumors in the ovaries.

15. A method for inhibiting metastasis of cancer in an animal, comprising administering the compound of claim 1 to the animal in amounts and at intervals effective to reduce or eliminate cancer metastasis.

16. A method for inhibiting cell migration in an animal, comprising administering the compound of claim 1 to the animal in amounts and at intervals effective to reduce or eliminate cancer cell migration.

17. A method of killing a cell in a tissue, comprising contacting the cell with the compound of claim 1 in amounts and at intervals effective to kill the cell, wherein the tissue comprises legumain.

* * * * *

UNITED STATES PATENT AND TRADEMARK OFFICE
CERTIFICATE OF CORRECTION

PATENT NO. : 7,608,591 B2 Page 1 of 1
APPLICATION NO. : 11/288978
DATED : October 27, 2009
INVENTOR(S) : Cheng Liu et al.

It is certified that error appears in the above-identified patent and that said Letters Patent is hereby corrected as shown below:

In column 1, lines 16-17, delete "(Grant Number P01 HL 16411 from the National Institutes of Health)." and insert -- (Grant Number P01 HL 16411 and R01 CA127535 from National Institute of Health, and W81XWH-05-1-0318 and W81XWH-07-1-0389 from Department of Defense). --, therefor.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO.       : 7,608,591 B2                                      Page 1 of 1
APPLICATION NO.  : 11/288978
DATED            : October 27, 2009
INVENTOR(S)      : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 412 days.

Signed and Sealed this

Twelfth Day of October, 2010

David J. Kappos
*Director of the United States Patent and Trademark Office*